US012691238B2

(12) United States Patent
Adametz et al.

(10) Patent No.: US 12,691,238 B2
(45) Date of Patent: Jul. 28, 2026

(54) INTERFACE FOR VENTILATOR

(71) Applicant: Loewenstein Medical Technology S.A., Luxembourg (LU)

(72) Inventors: Benjamin Adametz, Hamburg (DE); John Alberts, Reinbek (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1366 days.

(21) Appl. No.: 17/337,574

(22) Filed: Jun. 3, 2021

(65) Prior Publication Data

US 2021/0379307 A1 Dec. 9, 2021

(30) Foreign Application Priority Data

Jun. 6, 2020 (DE) .......................... 102020003438.1

(51) Int. Cl.
    *A61M 16/00* (2006.01)
    *G16H 40/63* (2018.01)
(52) U.S. Cl.
    CPC .......... *A61M 16/022* (2017.08); *G16H 40/63* (2018.01); *A61M 2205/3576* (2013.01); *A61M 2205/52* (2013.01); *A61M 2209/04* (2013.01)
(58) Field of Classification Search
    CPC ........ A61M 16/022; A61M 2205/3576; A61M 2209/04; G16H 10/65; G16H 40/63
    See application file for complete search history.

(56) References Cited

U.S. PATENT DOCUMENTS

| | | | | |
|---|---|---|---|---|
| 5,526,226 A * | 6/1996 | Katoh | ................... | G06F 1/1616 |
| | | | | 70/164 |
| 5,924,780 A * | 7/1999 | Ammon | .................. | G06F 1/181 |
| | | | | 312/223.2 |
| 2002/0144682 A1 | 10/2002 | Kruger et al. | | |
| 2002/0163777 A1 * | 11/2002 | Yu | ........................... | G06F 1/1632 |
| | | | | 361/679.3 |
| 2004/0230356 A1 * | 11/2004 | Namaky | ............. | G06F 11/2733 |
| | | | | 701/33.2 |
| 2007/0169776 A1 | 7/2007 | Kepler et al. | | |
| 2012/0075266 A1 * | 3/2012 | Shimizu | ................. | G16H 10/65 |
| | | | | 345/204 |
| 2013/0310756 A1 * | 11/2013 | Whalley | ................. | A61M 5/24 |
| | | | | 604/189 |
| 2017/0049978 A1 | 2/2017 | Berg et al. | | |
| 2018/0056020 A1 * | 3/2018 | Dimatteo | ............ | A61M 16/107 |
| 2018/0247712 A1 * | 8/2018 | Muhsin | ................ | A61B 5/7445 |
| 2019/0307981 A1 | 10/2019 | Ahmad et al. | | |
| 2020/0368468 A1 | 11/2020 | Liu et al. | | |

FOREIGN PATENT DOCUMENTS

| | | |
|---|---|---|
| WO | 2007038152 A2 | 4/2007 |
| WO | 2015167388 A1 | 11/2015 |
| WO | 2020082317 A1 | 4/2020 |

* cited by examiner

*Primary Examiner* — Brandy S Lee
*Assistant Examiner* — Sara K Toich
(74) *Attorney, Agent, or Firm* — Abel Schillinger, LLP

(57) ABSTRACT

A ventilator comprising a respiratory gas source and control systems, a housing with a receptacle and, lying at the base in a depression, an interface for receiving different data transfer sticks and data storage sticks.

20 Claims, 19 Drawing Sheets

INTERFACE FOR VENTILATOR

CROSS-REFERENCE TO RELATED APPLICATIONS

The present application claims priority under 35 U.S.C. § 119 of German Patent Application No. 102020003438.1, filed Jun. 6, 2020, the entire disclosure of which is expressly incorporated by reference herein.

BACKGROUND OF THE INVENTION

1. Field of the Invention

The invention relates to an interface for medical appliances, for example ventilators and anesthesia appliances and also combinations of the two aforementioned appliances for ventilation and anesthesia of patients. In the present invention, an interface is understood as a data transfer point that allows the specialist medical personnel to receive patient data and also to control and monitor actively, and in a partially automated manner, basic functions of the medical appliances at a location remote from the patient.

2. Discussion of Background Information

A ventilator is to be understood below as any appliance which supports the natural breathing of a user or patient, which takes over the ventilation of the user or patient and/or which serves for respiration therapy and/or influences the respiration of the user or patient in some other way. This includes for example, but not exclusively, CPAP and BiPAP appliances, anesthesia appliances, respiration therapy appliances, ventilators (for use in hospitals, in non-hospital environments or in emergencies), high-flow therapy appliances and coughing machines.

In previously known ventilators, remote data transfer is permitted by a modem implemented in the appliance or by Wifi/WLAN modules permanently installed on the electronic boards. The disadvantage of such a solution is that modems are difficult to exchange in the event of a defect and generally reflect the state of the art at the time of acquisition of the ventilator. An additional factor is that there are different network and approval standards in different states, and the permanently installed modem or module would therefore have to be adapted accordingly in each case. An additional factor is that ventilators are in most cases fully configured, i.e. all the available functions are installed in a medical appliance of this kind. This applies both to software applications at time of manufacture and also to hardware components and thus also to the aforementioned modem. Since ventilators are capital goods that are used over a long period of time, it is advisable to provide a possibility by which the data exchange can be kept as close as possible to the state of the art. This applies not only to the updating of the appliance software but also to the modem, which is in most cases purchased from suppliers. Once installed, it remains installed in the ventilator for the entire period of use. Replacement with an up-to-date modem version is complicated and costly and is therefore often avoided. It can even happen that modems become so obsolete that they are in fact no longer usable at all, and therefore this function is no longer available on the ventilator. However, should this function be required, it is first of all necessary to check whether a ventilator equipped with this functionality is available. In the worst case, replacement during ongoing ventilation is needed in order to allow the medical personnel the possibility of acquiring a suitably equipped appliance.

A modem is used when it is necessary or recommended to control and monitor the patient from a location remote from the patient. Here, remote from the patient signifies in particular the operation of a ventilator over quite a considerable distance, where proximity to the specialist medical personnel is not strictly necessary.

The use of a data transfer interface thus has the advantage that it can be equipped only as and when necessary with a data transfer stick, which can then be procured at any time, and the data transfer always takes place according to the latest state of the art. The use of a data transfer stick thus also makes it possible to save resources.

In view of the foregoing, it would be advantageous to have available a standardized interface for data transfer sticks which is easily accessible from outside.

SUMMARY OF THE INVENTION

The present invention provides a ventilator with a housing, at least one respiratory gas source, at least one control system and at least one interface, wherein the housing has a receptacle for the interface, and the receptacle is arranged with the interface in a depression of the housing. The depression is designed as a well, and the well has an opening, wherein at least two circumferential walls extend from the opening, in the direction of an interior of the ventilator, as far as to a base, and wherein the receptacle is arranged with the interface in the region of the base or of a circumferential wall of the depression. Here, a well is considered quite generally as a space which, starting from an opening, is at least partially surrounded to the sides by at least two walls and has a base lying opposite the opening. For example, it is possible for such a well to have only one open side, but it can also for example have three or more open sides.

In some embodiments of the ventilator, at least one circumferential wall has guide means in order to guide a data transfer stick and/or a data storage stick and to support same in the mounted state.

In some embodiments of the ventilator, the depression is closed by a lid.

In some embodiments of the ventilator, the depression is closed by a lid that closes substantially flush with the housing. Unless expressly stated to the contrary, closes substantially flush signifies that there is no or no appreciable offset/height difference between the surface that represents the outer face of the appliance and the surface that is represented by the outer face of the lid. An offset/height difference in the region of 2 mm, for example, can still be regarded as one that is substantially flush. This excludes any fittings on or structuring of the surface of the lid, for example for making it easier to open the lid, and any structuring of the outer face of the housing, for example by a certain roughness. The flush closure of the lid is also to be understood as meaning that the edges of the closed lid lie close to the edges of the housing. For example, there is a maximum spacing of 2 mm between the edges of the lid and the edges of the housing. For example, this spacing can also be embodied in the form of a groove.

In some embodiments of the ventilator, the lid is arranged movably relative to the housing and is secured on the housing.

In some embodiments of the ventilator, the lid has at least one fitting or a surface structuring in order to make it easier to open the lid. A fitting can be, for example, a narrow elevation that can be gripped with the fingers. A surface structuring can be obtained, for example, by a rough surface which generates a certain sliding resistance between fingers and lid surface. The arrangement of furrows, for example, on the surface of the lid can also provide such surface structuring.

In some embodiments of the ventilator, a mechanism is installed in the housing and/or the circumferential wall, which mechanism at least partially opens the lid when pressure is applied and returns it again to the starting position when renewed pressure is applied. For example, a lid can be mounted which, for example, closes flush with the housing and works without any extra fitting or the like but is still easy to open. For example, a kind of spring pressure element could be used which, when pressed in order to open the lid, moves a kind of pin by means of the spring, which in turn lifts the lid at least slightly, such that the latter could then be gripped. During closure of the lid, the pin and the spring can be returned to the original position by pressing.

In some embodiments of the ventilator, the lid is provided with a peripheral seal.

In some embodiments of the ventilator, the interface has a protection against spray water and against touching. The protection against spray water and against touching is intended to prevent the accidental admission of water and of foreign bodies into the interior of the ventilator. This would also avoid being able to reach into the interior of the ventilator through the interface. In some embodiments, the protection against spray water and against touching can be obtained by a suitably designed depression and/or lid, for example with a seal. A corresponding seal at the interface or in the region of the receptacle is also possible as a protection against spray water and against touching. In further embodiments, the protection against touching can attain class IP1X or higher and/or the protection against spray water can attain class IPX1 or higher.

In some embodiments of the ventilator, the receptacle, with the interface, and the depression are sealed off from the interior of the ventilator.

In some embodiments of the ventilator, the lid can be closed using a tool. For example, the lid could be closed using a screw which, in a position provided for this purpose, is screwed through the lid into the housing.

In some embodiments of the ventilator, the lid can be closed by a lock.

In some embodiments of the ventilator, the lid is designed as a slide.

In some embodiments of the ventilator, the lid, in the closed state, latches in a corresponding device in the circumferential walls and/or the housing edge and/or in/on the housing.

In some embodiments of the ventilator, the lid is connected to the housing by a hinge.

In some embodiments of the ventilator, the depression is arranged in the outer face of the housing, at a distance from the housing edge. Thus, for example, the well is surrounded on all four sides by a circumferential wall and is open only in the region of the opening. This means, for example, that a data transfer stick or a data storage stick can be inserted or removed only through the opening.

In some embodiments of the ventilator, the depression is part of the housing edge. This means, for example, that if no lid is present the depression is open on at least two sides—the opening and the part which is part of the housing edge.

In some embodiments of the ventilator, the depression extends at least partially over two longitudinal sides of the housing edge. For example, this would be the case if the depression is arranged at a corner of the housing and two of the circumferential walls are not present at this location.

In some embodiments of the ventilator, the interface permits contacting with a large number of different data transfer sticks.

In some embodiments of the ventilator, the interface permits contacting with a large number of different data storage sticks, for example USB sticks.

In some embodiments of the ventilator, the receptacle is recessed in the housing in such a way that a data transfer stick plugged in the receptacle and in the interface is arranged fully in the depression and terminates at most flush with the housing surface of the housing and does not protrude beyond the housing surface.

In some embodiments of the ventilator, the interface has engagement regions for fingers and/or thumbs in order to allow the data transfer stick and/or data storage stick to be pulled easily away.

In some embodiments of the ventilator, the interface and/or the receptacle and/or the depression has a removal device with a reset function.

In some embodiments of the ventilator, the data transfer stick is guided, by the actuation of the removal device, into a position in which it no longer terminates flush with the housing or is arranged inside the housing but instead at least partially protrudes from the housing.

In some embodiments of the ventilator, the interface connects the data transfer stick mechanically and electrically.

In some embodiments of the ventilator, the interface electrically and optionally mechanically connects the data transfer stick to an electronic circuit board present in the ventilator, directly or via a cable connection.

In some embodiments of the ventilator, the interface has a continuous current contact and/or an automatic current contact, wherein the automatic current contact is assigned a sensor which is designed to detect a mechanical occupancy of the interface.

In some embodiments of the ventilator, the interface is connected electrically conductively to a control unit of the ventilator and is designed for communication of data signals with the ventilator.

In some embodiments of the ventilator, the data transfer stick is designed as an insert module that can be inserted into the receptacle and plugged into the interface.

In some embodiments of the ventilator, the interface, through the connection of a data transfer stick, constitutes a transmitter/receiver which can be connected either to an ethernet and/or radio and/or GSM and/or UMTS and/or 4G and/or 5G network.

In some embodiments of the ventilator, the access to the data of a data transfer stick located in the interface is protected by password and/or hardware encoding.

In some embodiments of the ventilator, the interface can be used both for a data transfer stick and for a data storage on which patient data can be temporarily stored in order to further distribute these data over other channels.

In some embodiments of the ventilator, the interface and/or the receptacle and/or the base and/or the depression and/or the well and/or at least one circumferential wall has means and/or is designed to shield against electrical fields and radiofrequency waves.

In some embodiments of the ventilator, the interface and/or the receptacle and/or the base and/or the depression and/or the well and/or at least one circumferential wall is designed to permit electrical fields or waves only in the direction of the opening.

In some embodiments of the ventilator, the interface can also be used to transfer appliance software by means of a memory stick from one appliance to another appliance.

In some embodiments of the ventilator, the lid can be locked electronically.

In some embodiments of the ventilator, the electronic locking of the lid can be canceled by an authentication.

In some embodiments of the ventilator, the electronic locking of the lid is activated only when a data transfer stick and/or a data storage stick is connected to the interface.

In some embodiments of the ventilator, the receptacle is arranged in the lid, wherein the lid is connected to the housing.

In some embodiments of the ventilator, the lid extends at least over two longitudinal sides of the housing edge.

In some embodiments of the ventilator, the receptacle is arranged movably in the depression.

In some embodiments of the ventilator, the receptacle moves in the direction of the housing surface of the housing when the lid is opened.

In some embodiments of the ventilator, the receptacle is arranged on a cable which is electrically connected to the ventilator or to corresponding control units and is at least partially arranged in the depression, such that the receptacle can be at least partially pulled outside the depression.

In some embodiments of the ventilator, at least one further component and/or one further port is arranged in the depression in addition to the interface.

In some embodiments of the ventilator, the region of the interface in the depression is at least partially spatially separated from the further components and/or ports by an at least partially formed partition wall.

In some embodiments of the ventilator, the depression is partially concealed by the housing surface.

In some embodiments of the ventilator, the receptacle with the interface is arranged in or on one of the circumferential walls, wherein the depression, in the region of the circumferential wall in or on which the receptacle is arranged, is concealed by the housing surface.

In some embodiments, at least one foam element is arranged in the depression and/or on the lid. Such a foam element can be used, for example, to retain the data transfer stick or the data storage stick plugged into the interface or to fix it against movements that might lead to accidental release of the connection between data transfer stick and data storage stick.

In some embodiments of the ventilator, at least one spring element for fixing the data transfer stick or the data storage stick is mounted on the lid and/or in the depression.

The invention also provides a system for establishing a wireless connection, comprising at least one ventilator, at least one interface, at least one data transfer stick and at least one lid, wherein the interface is arranged in a depression, and the data transfer stick is connected removably in the depression to the interface, wherein the depression can be closed with the lid.

Subject matter of the present invention therefore also is an interface on the ventilator, which interface, on the one hand by virtue of its shape and characteristics and on the other hand by virtue of the possibility of using a large number of different data transfer sticks conforming to the general standards, is able to receive and transmit data. When selecting the precise position on the ventilator, consideration should be given in particular to good accessibility.

It is thus possible to dispense with a modem that is not accessible from the outside.

Since the ventilators equipped with the interface according to the invention are generally used in intensive care medicine and in a homecare environment, operating errors and disturbances associated with the use of the interface must be ruled out as far as possible. In this context, operating errors are understood as disturbances which are due to an error on the part of the specialist medical personnel. Disturbances are in principle all further errors that cannot be attributed to an operating error and that are caused by external influences.

The interface should therefore comply with the high safety demands placed on medical appliances, but without having to compromise on operating comfort and functionality.

The interface should therefore be arranged on the ventilator at a place that can be easily accessed by the operating personnel and by technical personnel, and it should afford the possibility of easy plugging. In one illustrative embodiment, the interface could accordingly lie in the housing surface, delimited by four circumferential walls, but it could also be located in the region forming the housing surface edge and thus only be delimited by three circumferential walls. It would likewise be conceivable to place the interface in a corner region of the housing. Consequently, in this case only two circumferential walls would form a lateral boundary.

Mechanical access to the data transfer stick should be readily possible for authorized persons, irrespective of the precise nature, i.e. length, width, height, size, of the data transfer stick. It is also plugged in the housing such that it advantageously does not protrude above the housing edge, so as to prevent it from being accidentally damaged or removed by mechanical forces. In a further advantageous embodiment, it is also possible to secure the stick against unauthorized removal and manipulation from outside.

In principle, it should generally be possible for authorized persons to remove the data transfer stick without tools. In some embodiments, however, removal can also be possible by use of a tool.

A system for blocking the data transfer stick would also be conceivable in this context, for example similar to the functionality, used in automatic vehicles, for preventing the release of the key as long as the selector lever is not in park mode. Release of the data transfer stick or data storage stick for the purpose of removal is thus possible only when the specialist medical personnel have provided authentication and are thus authorized to remove the stick from the interface.

However, besides the abovementioned electromechanical securing of the stick, purely mechanical securing arrangements are also possible, such as closure of the well with a lid in different embodiments.

In order to protect the well and in particular the contacts from moisture, the lid is equipped with a peripheral rubber seal. Here, the peripheral rubber seal does not necessarily have to be mounted on the lid side.

This is achieved by an interface sitting in a depression of different design and extent.

The aim of all of the aforementioned measures is to ensure safety in the use of the functionalities of the data transfer stick, without needlessly making handling more difficult.

This is further achieved by a cover which is connected permanently to the housing of the medical appliance and which on the one hand prevents the unauthorized removal of the stick and also, by means of peripheral sealing lips integrated in the cover or in the housing, affords protection against ingress of water or moisture.

BRIEF DESCRIPTION OF THE DRAWINGS

The proposed interface in a ventilator is explained in more detail below with reference to a number of different and in some cases greatly simplified drawings. In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
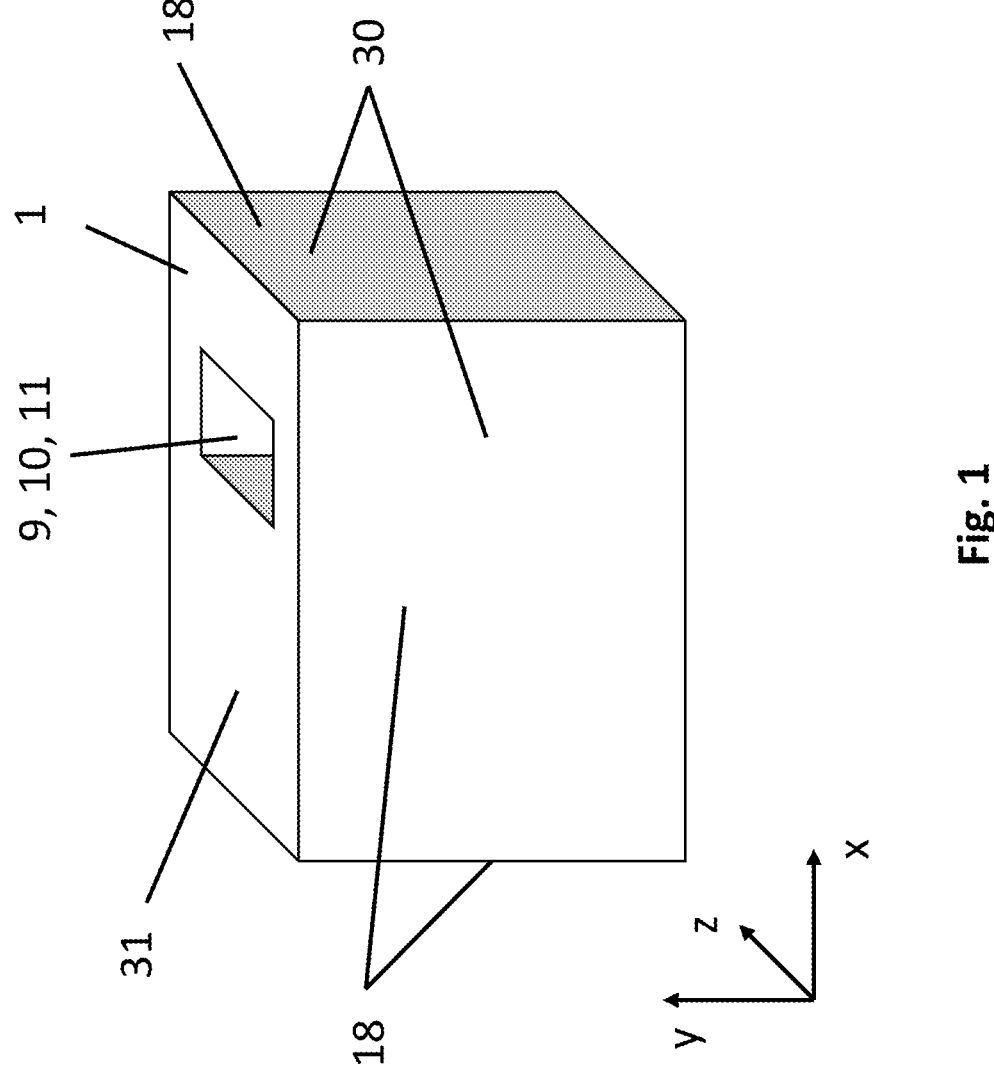
FIG. 1 shows an illustrative embodiment of the claimed ventilator in a simplified perspective view, with the housing 1 and with the depression 9 configured as a well 10.

FIG. 1 shows a greatly simplified schematic view of an illustrative embodiment of the ventilator or of the housing 1 in a perspective view. The depression 9, which is designed for example as a well 10 and in which the interface 6 is arranged, is arranged here in the side of the housing 1 designated as housing surface 31. Adjoining this housing surface 31 there extends the housing edge 18, which at the same time also constitutes the outer faces 30. The arrangement of the depression 9 on the top of the housing designated as housing surface 31 is to be understood here only as an example. The depression 9 can also be arranged on one of the outer sides or on the underside of the housing 1. Toward the housing surface 31, the depression has an opening 11 through which, for example, a data transfer stick 19 or a data storage stick 20 can be introduced into the depression. A data transfer stick 19 can be a WLAN stick, for example, which permits a connection to wireless networks, or also a so-called surfstick which, for example, can permit a connection to 4G/5G networks. Other configurations of the data transfer stick 19 are also conceivable and possible here, for example for Bluetooth or LPWAN or other wireless connections. To this end, for example, the depression 9 has guide means which, for example, guide the data transfer stick 19 into the receptacle 7 or the interface 6. These guide means can additionally be configured such that they support or retain the data transfer stick 19 or the data storage stick 20 in the mounted state. For example, the depression 9, with the interface 6, or the opening 11 should also be arranged to be easily accessible during the operation of the ventilator. The greatly simplified view of the example of the housing 1 as a cuboid serves for illustrative purposes only and does not exclude other possible forms. The housing 1 can additionally assume any other conceivable shape.

Figure 2:
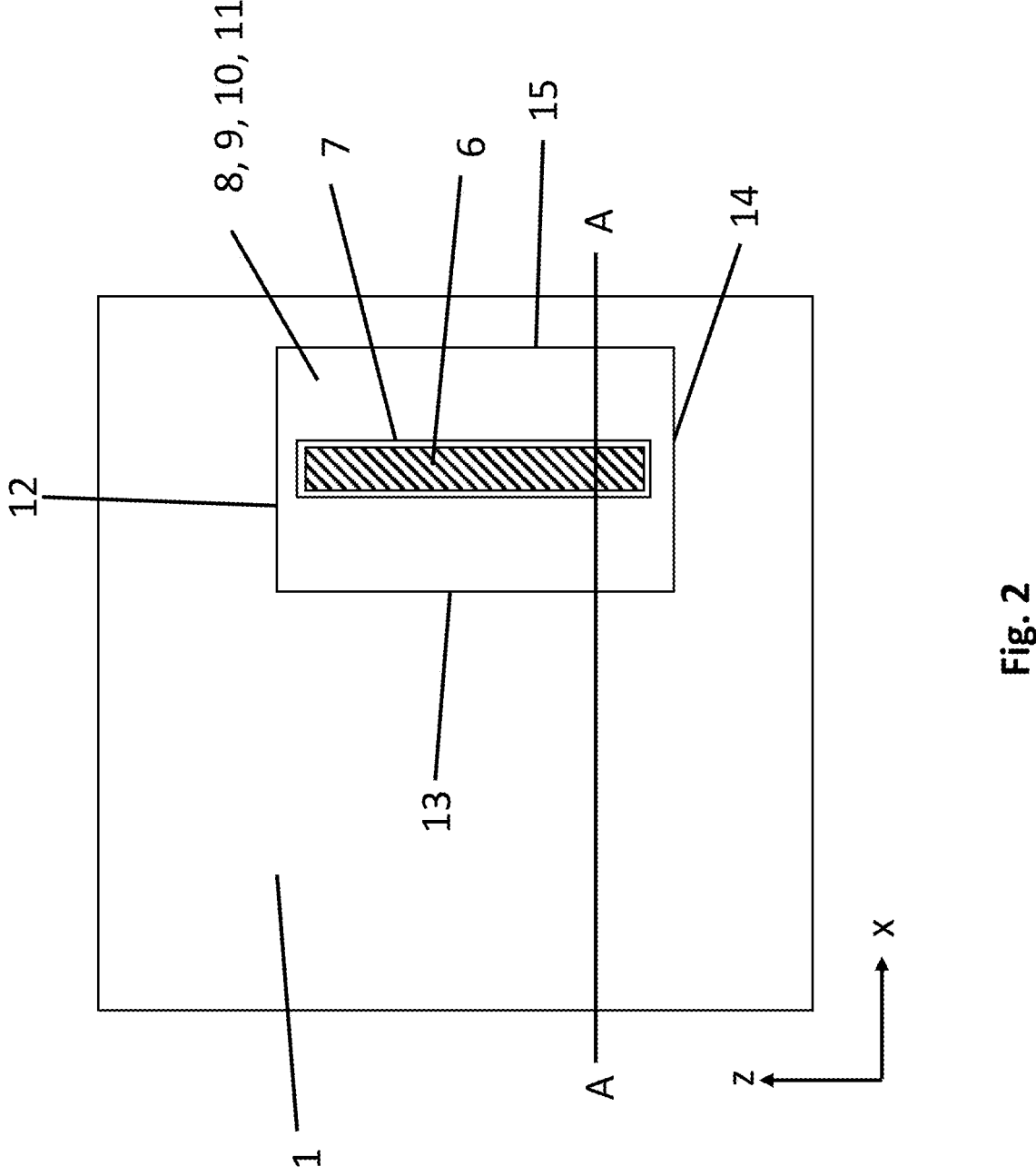
FIG. 2 shows a plan view of the ventilator from FIG. 1, with the interface 6 in the receptacle 7.

A plan view of the example of the housing 1 is shown in FIG. 2. The depression 9 configured as a well 10 is arranged spaced apart from the housing edge 18 and is in this case delimited at the sides by circumferential walls 12, 13, 14, 15 which extend from the opening 11, in the direction of the interior of the ventilator, as far as the base 8. In the region of the base 8, a receptacle 7 with the interface 6 is arranged for example. The interface 6 is for example configured such a large number of possible data transfer sticks 19 and data storage sticks 20 can be connected to the interface. For example, the interface has a USB port and/or a lightning port. The interface 6 permits for example a communication of data signals between the ventilator and the data transfer stick 19 or data storage stick 20. In addition to the electrical connection, the interface 6 also constitutes in addition a possibility of mechanical connection to a data transfer stick 19 or a data storage stick 20. The receptacle 7 can be designed in different variants. For example, while not excluding other configurations, the receptacle can be an aperture which is provided in the base 8 leading to the interior of the ventilator and which surrounds the interface 6. Between the receptacle 7 and the actual interface 6, seals can also be fitted for example, such that a protection against spray water and against touching can be ensured. In addition to an aperture in the base 8, it is also possible for example that the receptacle 7 and the interface 6 protrude slightly above the base 8 and jut into the space defined by the depression 9. Moreover, the receptacle 7 can also be designed such that it additionally supports or completely assumes the retention of an inserted data transfer stick 19 or data storage stick 20. The depression 9 is shown by way of example with a rectangular cross-sectional profile. Furthermore, however, the cross-sectional profile can also assume oval or round shapes or also have a polyhedral shape or a free form. Starting from the opening 11, the cross-sectional shape can also vary in the direction of the base 8. For example, the cross-sectional area in the region of the opening 11 can be larger and decrease in the direction of the base 8. This is the case, for example, when the depression has additional engagement regions.

Figure 3:
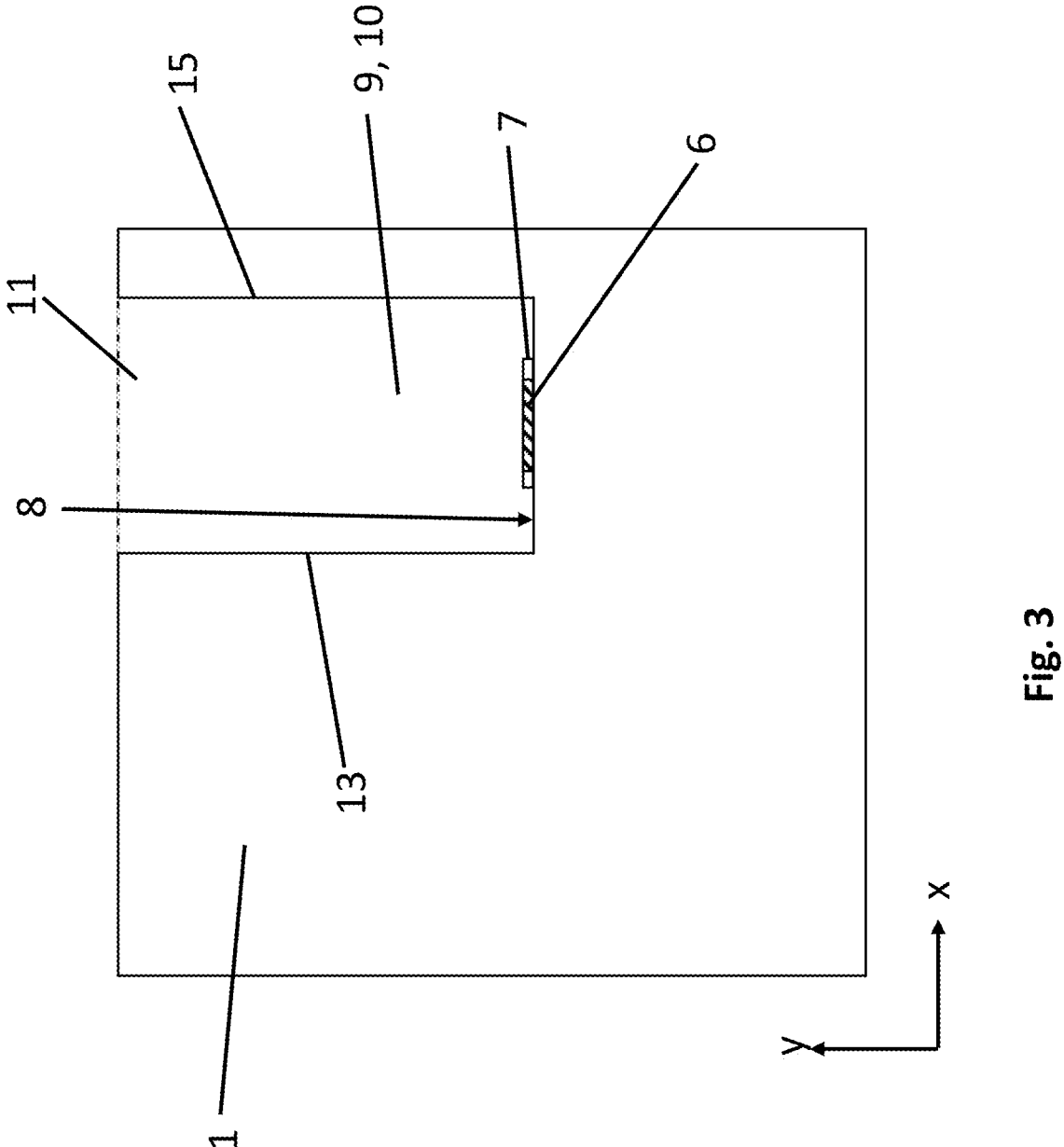
FIG. 3 shows cross section A-A through the housing 1 from FIG. 2.

The cross section A-A through the illustrative embodiment of the housing 1 from FIG. 2 can be seen in FIG. 3. For example, in the embodiment shown, the receptacle 7 and the interface 6 are configured such that they protrude slightly into the space of the depression and are arranged on the base 8. The upper edge of one of the circumferential walls 12, 14 is indicated by the broken line at the opening 11. The cross-sectional profile along the direction from the opening 11 to the base 8 (y direction) is rectangular, for example. Furthermore, however, other cross-sectional profiles of the depression are also conceivable. On the circumferential walls 12, 13, 14, 15, for example, guide means can additionally be mounted which guide the insertion of a data transfer stick 19 or a data storage stick 20 and support these in the mounted state, i.e. when plugged into the interface 6.

Figure 4:
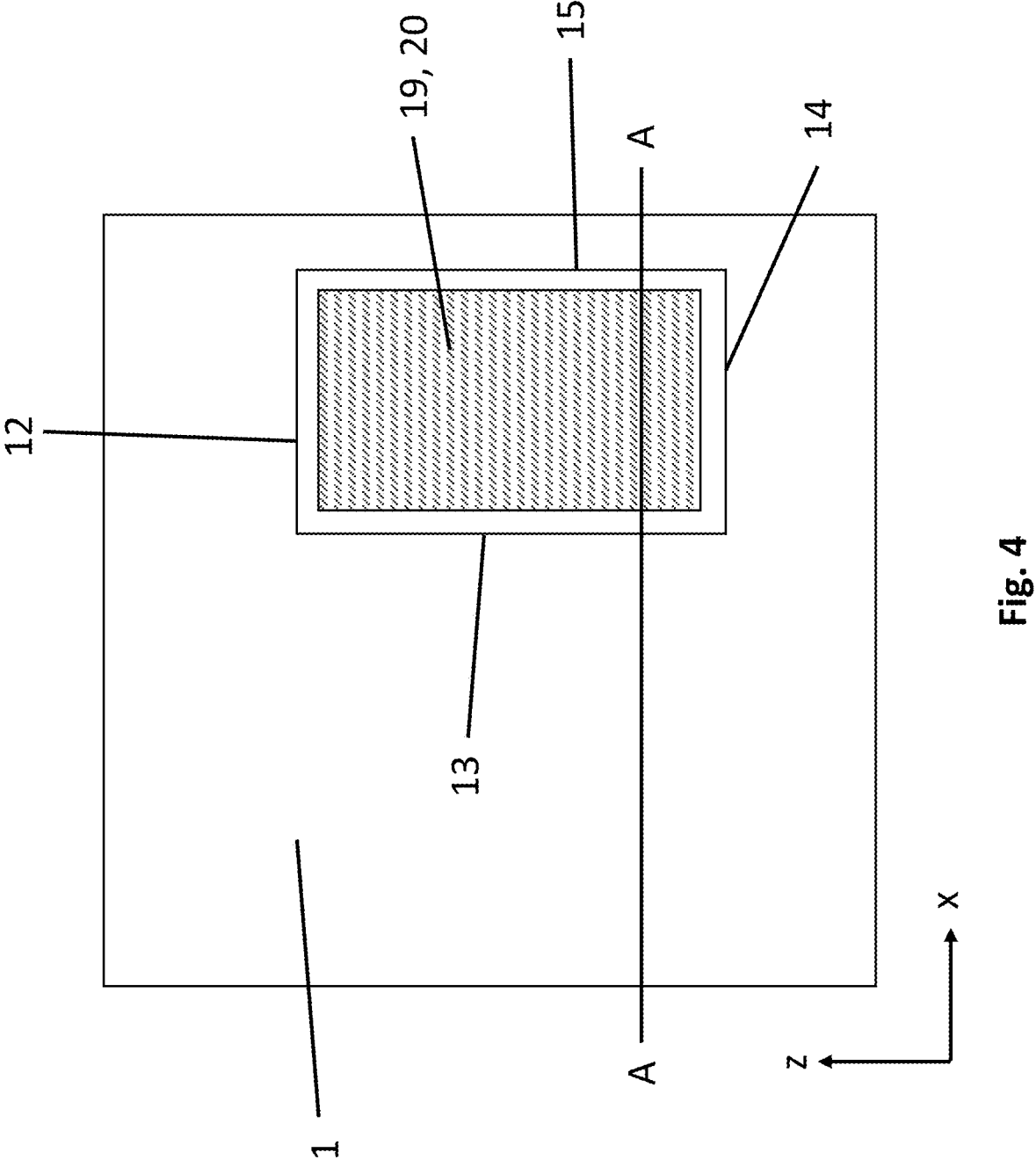
FIG. 4 shows a plan view of an illustrative embodiment of the ventilator, with data transfer stick 19 or data storage stick 20.

During use of the interface 6, a data transfer stick 19 or a data storage stick 20 is connected to the interface 6, as is shown by way of example in FIG. 4. By the connection of the data transfer stick 19 to the interface 6, a transmitting/receiving arrangement, for example, is formed which can be connected, for example, to an ethernet and/or radio and/or GSM and/or UMTS and/or 4G and/or 5G network. The depression 9 is dimensioned such that a data transfer stick 19 or a data storage stick 20 can be received completely by the depression. In some embodiments, it is also possible that the depression 9 is dimensioned such that the data transfer stick 19 or the data storage stick 20 protrudes partially through the opening 11 above the surface 31 of the housing.

Figure 5:
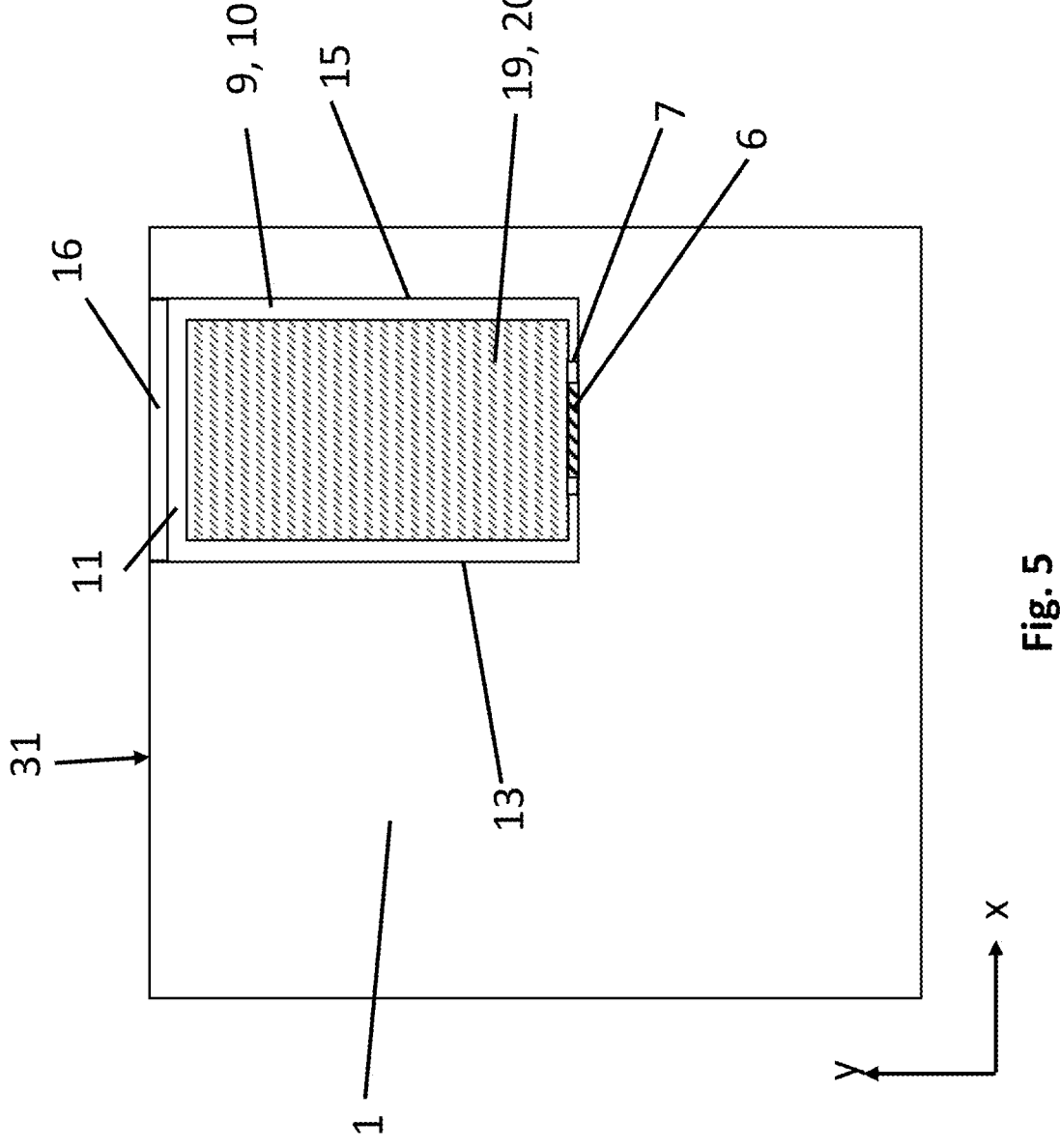
FIG. 5 shows cross section A-A through the housing 1 from FIG. 4, with lid 16.

FIG. 5 shows the cross section A-A of the example of the housing 1 from FIG. 4. For example, a data transfer stick 19 or a data storage stick 20 is connected in the receptacle 7 to the interface 6. The depression 9 is for example dimensioned such that the inserted data transfer stick 19 or data storage stick 20 does not protrude above the surface 31 of the housing 1. For example, the depression 9 is closed in the region of the opening 1 by lid 16. In some embodiments, the lid 16 can for example also close flush with the housing 1. The lid 16 is for example connected permanently to the housing 1. Such a connection can be achieved, for example, by a hinge 26. A simple connection by a type of band between housing 1 and lid 16 can also constitute a permanent connection. In some illustrative embodiments, the lid 16 can be closed firmly on the depression 9. For example, the lid 16 or the housing 1 can be assigned a lock, with which the lid 16 can be closed with a key. Such a closure is an example of a measure by which the data transfer stick 19 or the data storage stick 20 is protected against unauthorized removal. Alternatively, the lid 16 can for example also be designed to be closeable with other tools. For example, the screwing of a screw into corresponding devices in lid 16 and housing 1 can close the lid 16 firmly on the depression 9.

The lid 16 can for example also be coupled to the receptacle 7 and interface 6 such that, upon opening of the lid 16, the receptacle and interface 6 are moved in the direction of the opening 11. For example, when the lid 16 is fully opened, a data transfer stick 19 or data storage stick 20 plugged into the interface 6 protrudes at least partially above the housing surface 31.

Figure 6:
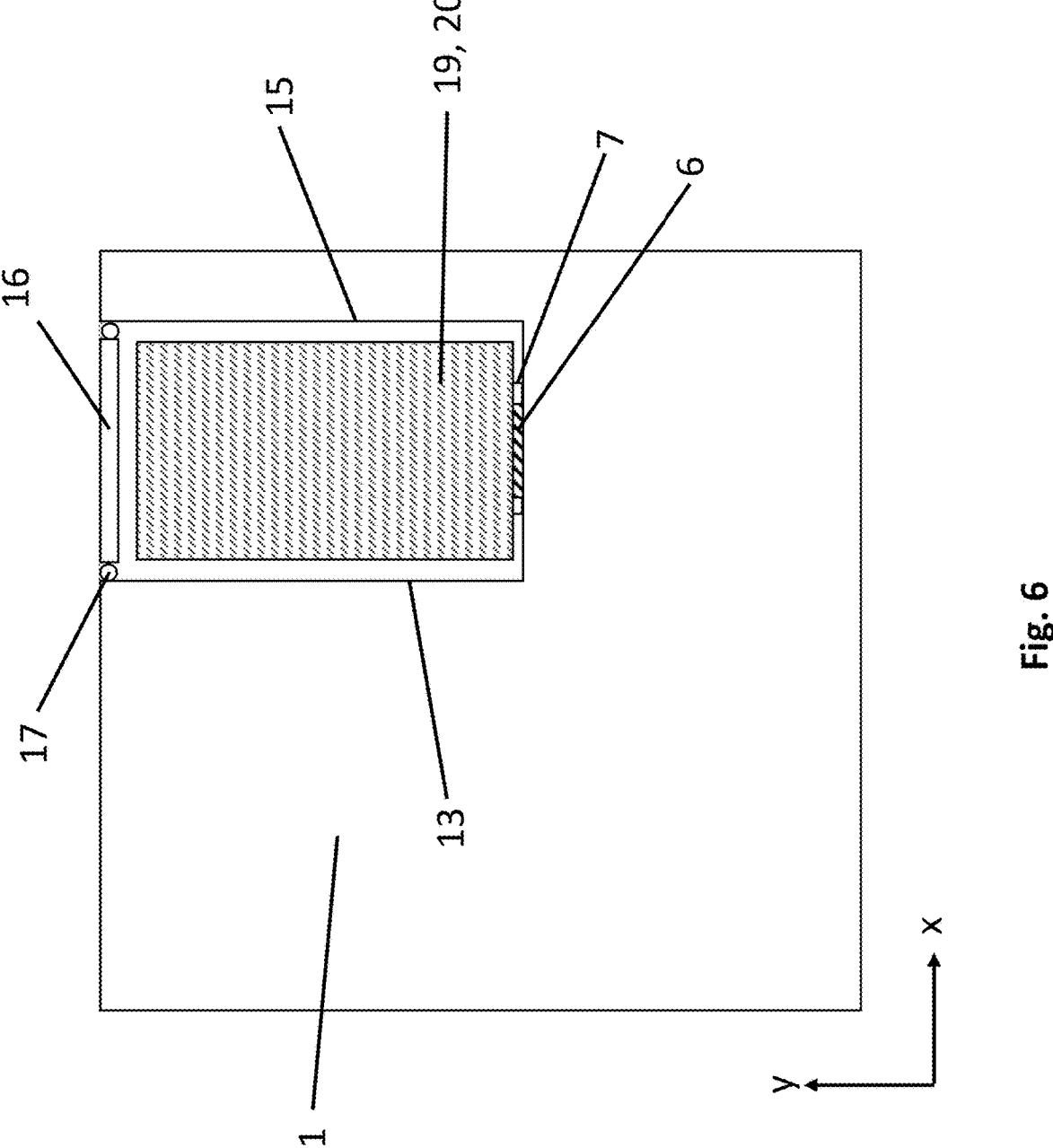
FIG. 6 shows cross section A-A through the housing 1 from FIG. 4, with lid 16 and peripheral seal 17.

An illustrative embodiment of the housing 1 with lid 16 is also shown in FIG. 6. Here, the lid 16 is equipped for example with peripheral seals 17. With the aid of these seals, it is possible to protect the interface 6 against spray water and against being touched. The seal 17 is shown here for example as part of the lid 16, but it can also be part of the opening 11 or can generally be arranged as part of the depression 9.

For example, lid 16 and depression 9 are matched to each other such that a seal 17 arranged on the lid 16 or on the depression 9 contributes to the depression 9 and thus also to the interface 6 being sealed off from the exterior of the ventilator. In FIG. 6, the seal 17 is arranged for example between the circumferential walls 12, 13, 14, 15 and the lid 16. However, it is also conceivable for the seal 17 to be arranged along the circumferential walls on an edge or collar on or in which the seal 17 is firmly inserted. When the lid 16 is closed, it then bears on the peripheral seal 17 or for example is pressed onto the seal 17. When the lid 16 is closed, this seal then presses for example against the circumferential walls of the depression 9 or is pressed onto an edge or collar that is arranged peripherally along the circumferential walls. Alternatively, the lid 16 itself can also be designed as a seal 17. To this end, the lid is made for example of a soft plastic, for example silicone, and can be pressed sealingly into the opening 11 of the depression. In a design of the lid 16 in which it closes flush for example, a fitting 23 designed as a tab for example could be mounted on the lid 16, in order to be able to use the tab to pull the lid out of the opening 11. The depression 9 is for example dimensioned such that the data transfer stick 19 or data storage stick 20 can be inserted spaced apart from the lid 16. This spacing between data transfer stick 19 or data storage stick 20 and lid 16 should at least be so great that the lid 16 does not exert any mechanical load on the data transfer stick 19 or the data storage stick 20. It is also possible for there to be a spacing between lid 16 and data transfer stick 19 or data storage stick 20 that is not apparent to the eye. In some embodiments, the lid 16 for example presses lightly on the data transfer stick 19 or the data storage stick 20, such that the latter is supported in the housing. For example, a retention element, in which the data transfer stick 19 for example is inserted, is mounted on the lid and/or in the well such that the data transfer stick 19 is firmly clamped or pressed in. For example, this retention element can be an elastic foam element which is mounted for example on the inner face of the lid 16 and/or in the well 10. If the interface 6 is arranged for example on the base 8 of the well 10, a foam element can be mounted for example on the inner face of the lid 16. The foam element is in this case designed such that, when the lid 16 is closed with the data transfer stick 19 or data storage stick 20 inserted, the lid 16 or the foam element presses on the data transfer stick 19 or the data storage stick 20. In the process, the foam element for example deforms such that it essentially conforms to the data transfer stick 19 or the data storage stick 20 but on the other hand also contributes to fixing. Instead of a foam element, it is also possible, for example, for a spring element to be mounted on the inner face of the lid 16, which spring element likewise can exert quite a light pressure on an inserted data transfer stick 19 or data storage stick 20 for fixing purposes.

Figure 7:
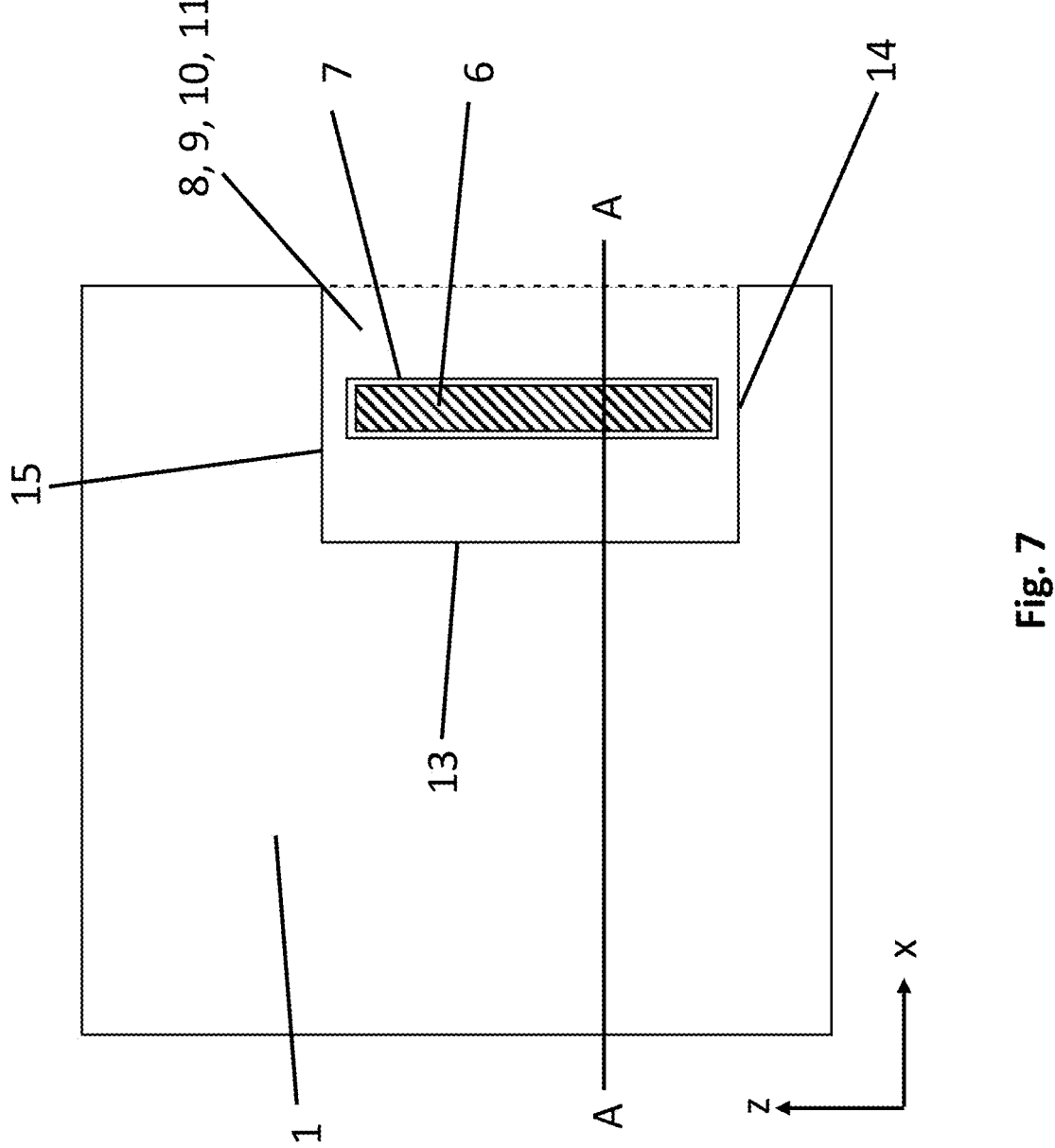
FIG. 7 shows a plan view of an illustrative embodiment of the ventilator, with the depression 9 as part of the outer face 30 in the housing edge 18 of the housing 1.
Figure 8:
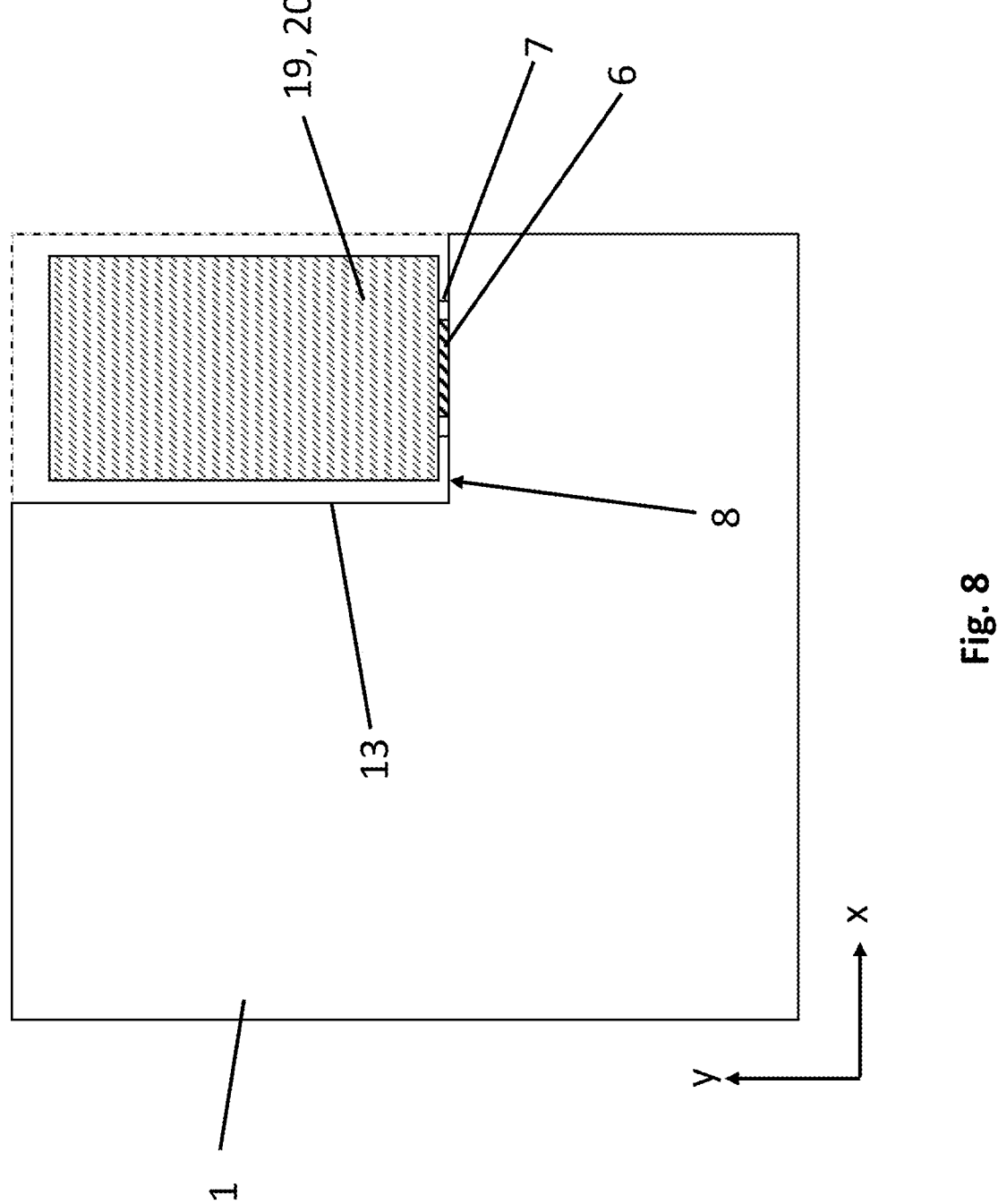
FIG. 8 shows cross section A-A through the housing 1 from FIG. 7, with data transfer stick 19 or data storage stick 20.

In some illustrative embodiments, the depression 9 is arranged at least partially in an outer face 30 of the housing edge 18. Such an illustrative embodiment is shown in a plan view in FIG. 7, while FIG. 8 shows the cross section A-A from FIG. 7. Through the position of the depression in the housing edge 18, the depression 9 is open to the surface 31 of the housing 1 and also to an outer face 30 in the housing edge 18. If, as is shown by way of example in FIG. 8, a data transfer stick 19 or a data storage stick 20 is plugged in the interface 6, it is accessible from two sides.

Figure 9:
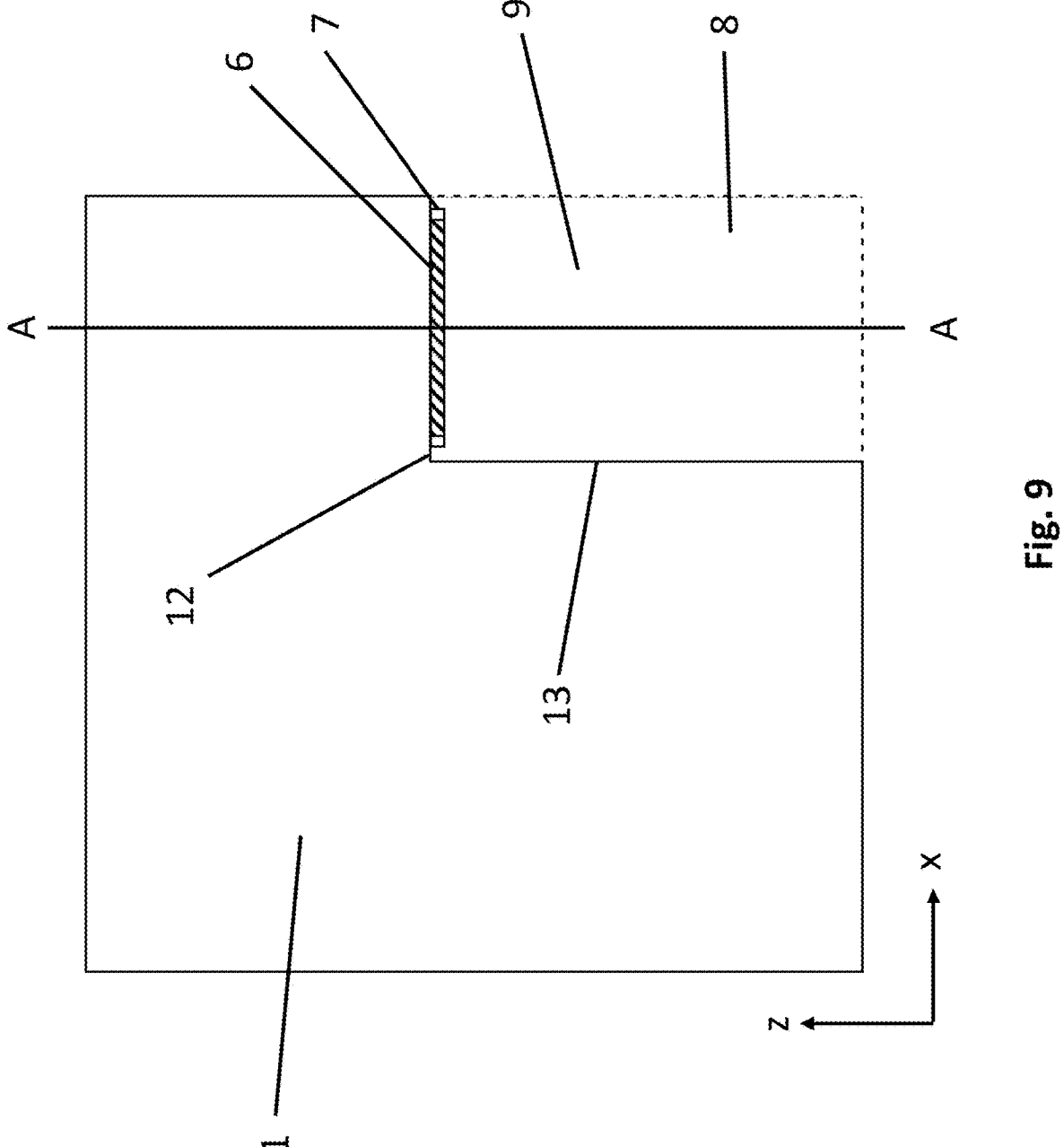
FIG. 9 shows a plan view of an illustrative embodiment of the ventilator, with the depression 9 as part of two outer faces 30 in the housing edge 18.
Figure 10:
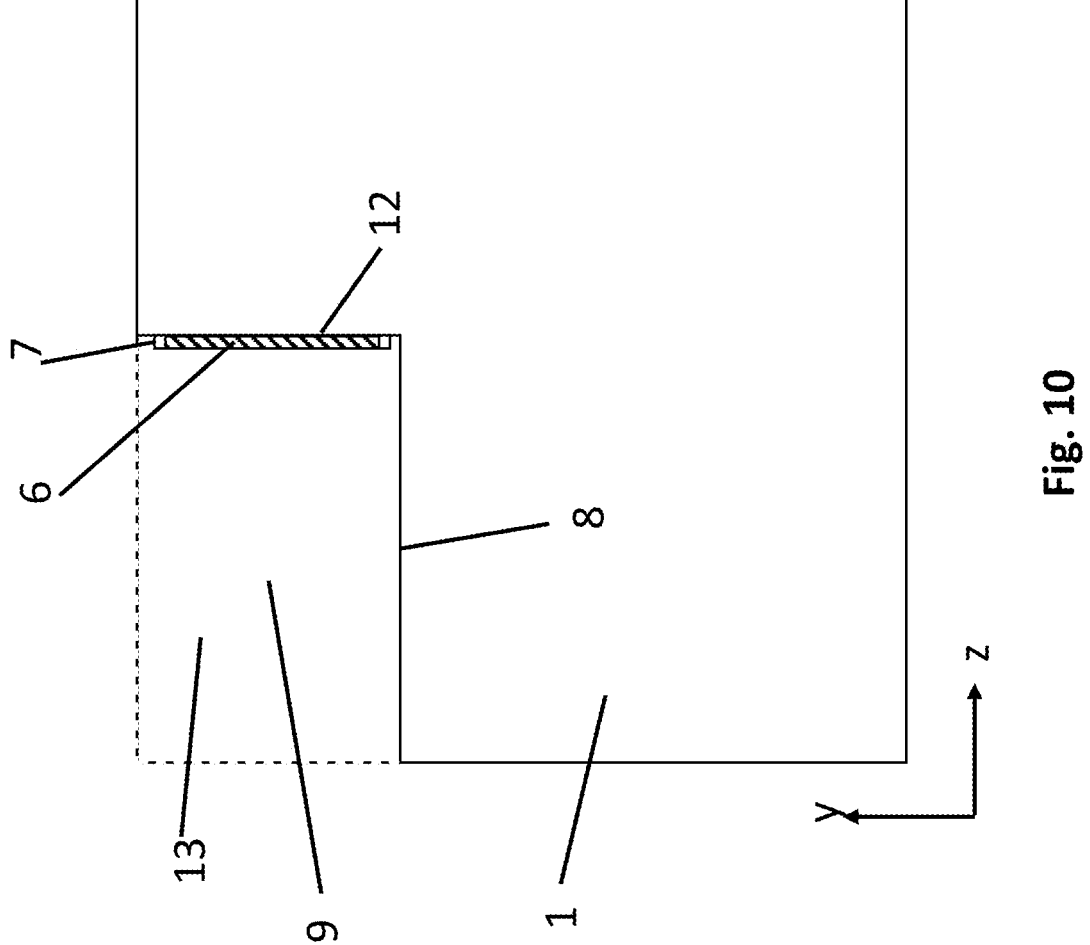
FIG. 10 shows cross section A-A through the housing 1 from FIG. 9.
Figure 11:
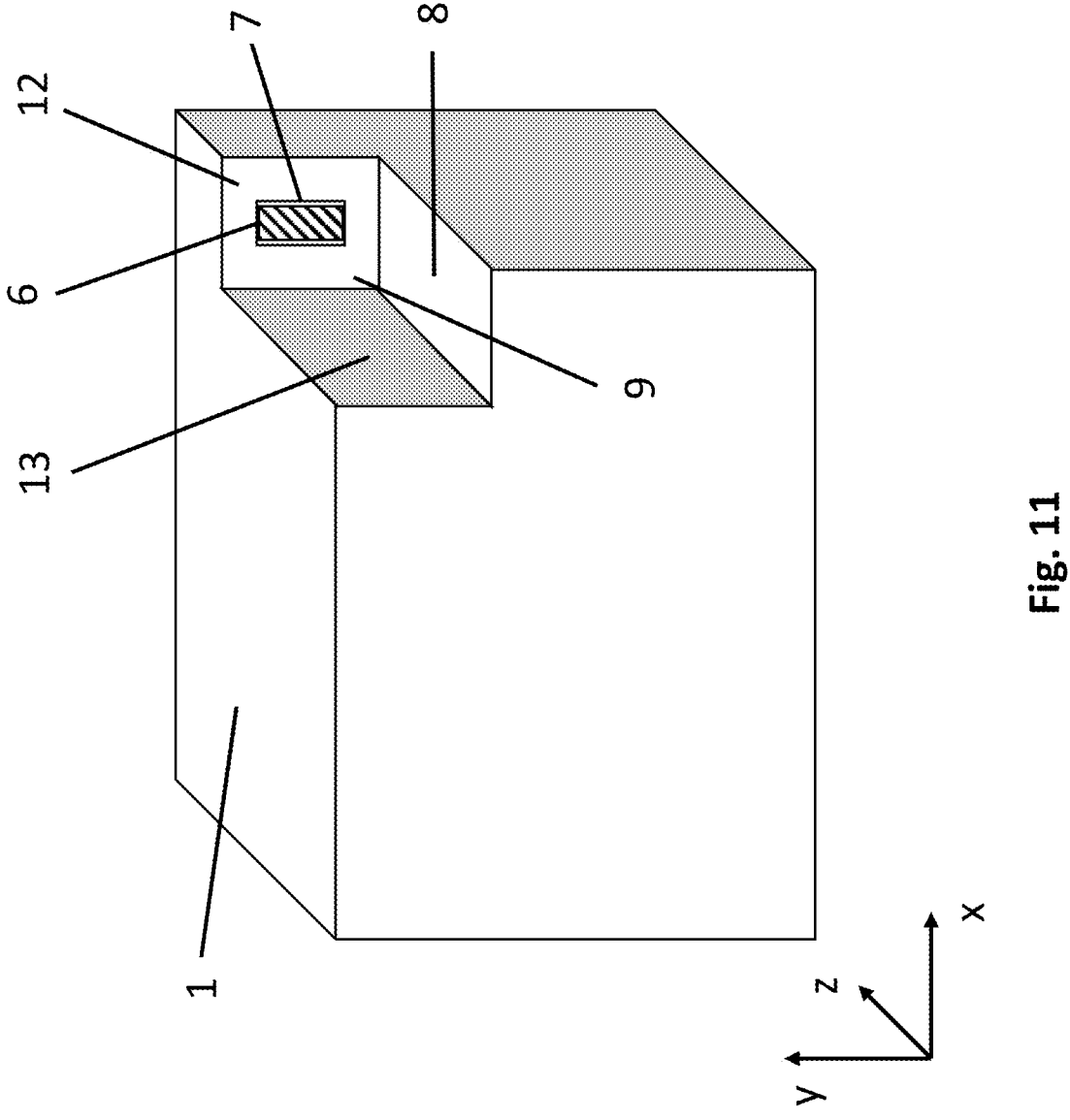
FIG. 11 shows a perspective view of an illustrative embodiment of the ventilator, 18.

In the illustrative embodiments of the housing 1 shown in FIGS. 9, 10 and 11, the depression 9 is arranged in a corner of the housing 1 and is thus part of two outer faces 31 of the housing edge 18. FIG. 9 shows a plan view of the housing 1, while FIG. 10 shows a schematic view of its cross section A-A. To illustrate the position of the depression 9 in a corner of the housing 1, the housing 1 is shown in a greatly simplified perspective view in FIG. 11. In the embodiment shown in FIGS. 9 to 11, the receptacle 7 with the interface 6 is arranged in the circumferential wall 12. It is likewise possible to arrange the receptacle 7 with the interface 6 in another circumferential wall or the base 8. In order to produce a protection against spray water and/or against touching, a lid 16 can for example also be mounted on the depression 9, such that all three open sides are closed. The lid 16 can in this case be connected movably and permanently to the housing 1 or can also be designed to be completely removable. For example, the lid 16 is designed to be completely removable and, upon closure of the depression 9, can be releasably connected to corresponding devices in the housing 1 and on the lid 16, for example by latching or by other ways and means. In another illustrative embodiment, the lid 16 can also be connected to the housing 1 at a side via a hinge 26. In further embodiments, the permanent connection between housing 1 and lid 16 can be realized by a kind of band.

With the receptacle 7 with the interface 6 positioned in one of the circumferential walls 12, 13, 14, 15 of the depression 9, one or more spring elements can be mounted for example on the opposite side—in the lid 16 or the opposite circumferential wall—in order to support the retention of the data transfer stick 19 or of the data storage stick 20 in the interface 6. Upon insertion of a data transfer stick 19 for example, the spring elements are for example first of all compressed by the data transfer stick 19, such that plugging of the data transfer stick 19 into the interface 6 is permitted. As the data transfer stick 19 is plugged into the interface 6, the spring elements partially expand outward again but do not reach their original expansion. As a result of the further attempt by the spring elements to assume the original expansion again, the data transfer stick 19 for example is additionally pressed into the interface 6 and thereby retained. A combination of different methods of retaining and fixing the data transfer stick 19 or the data storage stick 20 in the interface 6 or the depression 9 is likewise conceivable. For example, the spring elements described here can be arranged in the circumferential wall 12, 13, 14, 15 lying opposite the interface 6, and one or more foam elements can additionally be mounted on the inner face of the lid 16.

Figure 12:
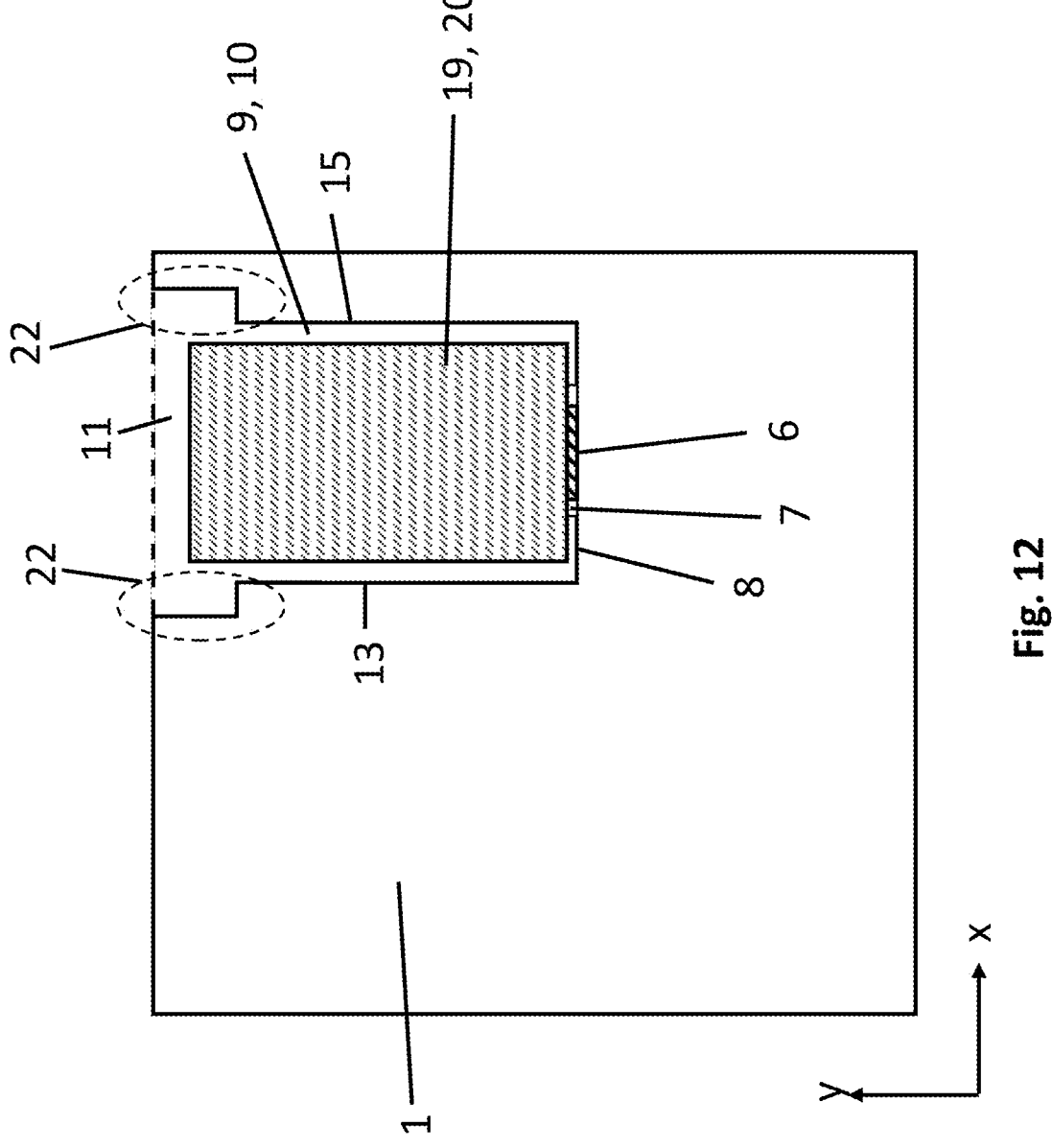
FIG. 12 shows a cross section through an illustrative embodiment of the ventilator, with housing 1 and with engagement regions 22 at the depression 9.

FIG. 12 shows a schematic view of an illustrative embodiment of the housing 1 of the ventilator, wherein the depression 9 has engagement regions 22. These engagement regions 22 are realized, for example, by a widening of the depression 9 in the region of the opening 11. In this way, the region of the opening 11 opposite the part of the depression 9 designed as well 10 is widened such that it is possible for one or more fingers and/or thumbs to be placed around the data transfer stick 19 or a data storage stick 20. For example, these engagement regions 22 are dimensioned such that a data transfer stick 19 for example protrudes partially above the edge between the circumferential wall 12, 13, 14, 15 of the depression 9 and the engagement region 22. For example, the engagement regions 22 can also be linked to other functions, for example devices for closing the lid 16.

Figure 13:
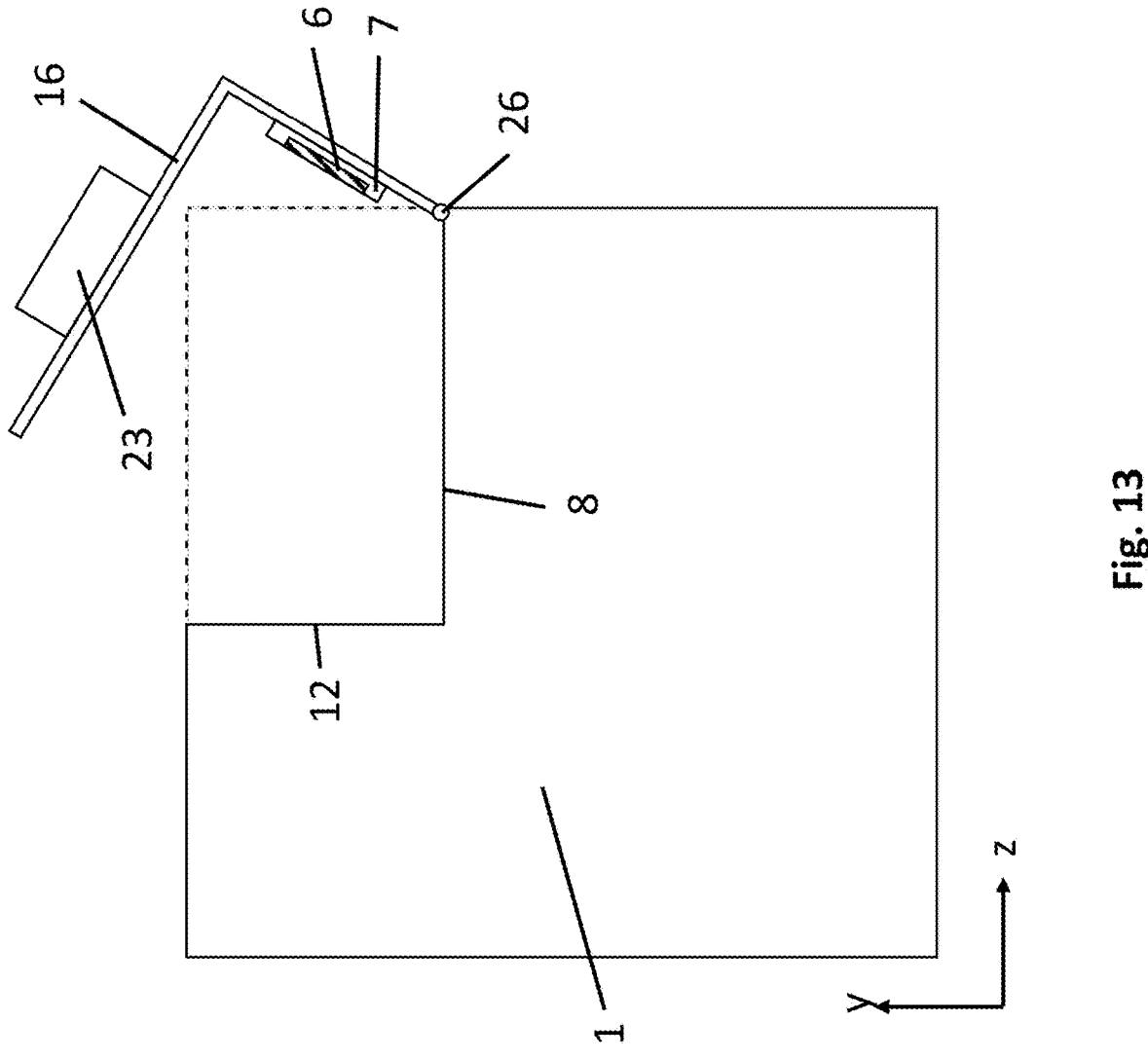
FIG. 13 shows a cross section through an illustrative embodiment of the ventilator, with a receptacle 7 with interface 6 arranged in the lid 16.

In addition to the receptacle 7 with the interface 6 being arranged in the base 8 or one of the circumferential walls 12, 13, 14, 15 of the depression, it is also possible for the receptacle 7 with interface 6 to be arranged in the lid 16. Such an illustrative embodiment is shown in FIG. 13. The lid 16 is here connected to the housing 1 by a hinge 26, for example. The receptacle 7 with the interface 6 is mounted on one side of the lid 16. Thus, for example, the data transfer stick 19 or the data storage stick 20 can be plugged into the opened lid 16 and, by closure of the lid 16, is guided into the depression 9. For example, the lid 16, or more precisely the interface 6 arranged in the lid 16, is connected to the housing 1 or the ventilator not only mechanically but also electrically. In the absence of an electrical connection between lid 16 or interface 6 and the ventilator, the interface 6 would accordingly be unable to function, since data would not be able to be exchanged between data transfer stick 19 or data storage stick 20 and the ventilator. For example, the lid 16 is connected captively or permanently, but movably, to the housing 1. In an illustrative embodiment in which the lid 16 is connected to the housing by a kind of band, this band can also at the same time assume the function of a cable for the electrical connection between lid 16 and ventilator. The lid 16 can also be designed separately, i.e. not permanently connected to the housing 1. If the receptacle 7 with the interface 6 is situated for example in/on the lid 16, then the lid 16 and the housing 1 or the ventilator would need to have devices such that an electrical connection can be produced between lid 16 and ventilator when the lid 16 is mounted or closed.

For example, the lid 16 also has a fitting 23. This fitting 23 can be mounted for example in the form of a web or a thin projection on the outer face of the lid 16, i.e. on the face that does not lie in the depression 9 when the lid 16 is closed. Such a fitting can be used, for example, by being gripped in order to open the lid 16.

Figure 14:
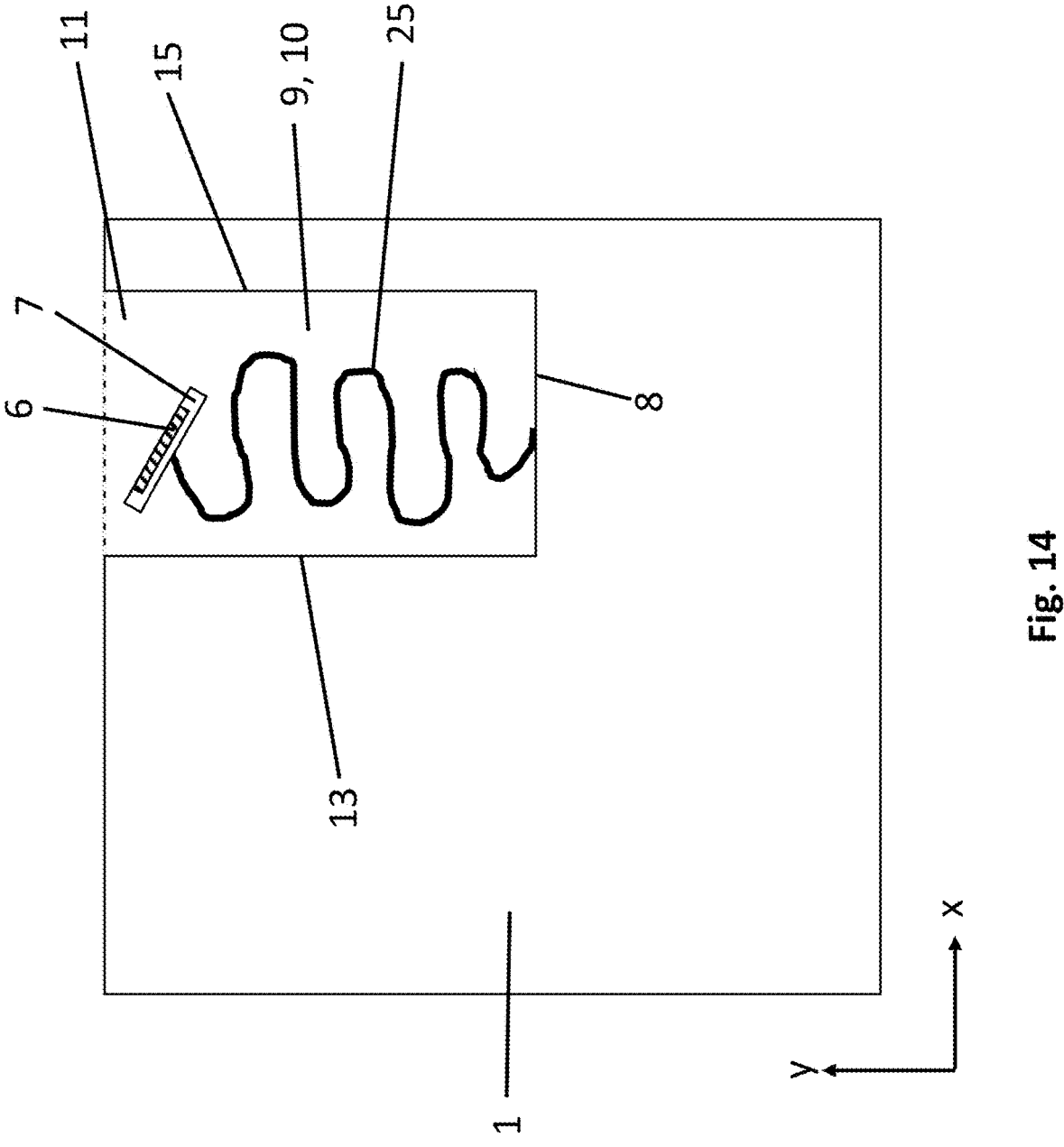
FIG. 14 shows a cross section through an illustrative embodiment of the ventilator, with a receptacle 7 with interface 6 arranged on a cable 25.

FIG. 14 shows a schematic view of an illustrative embodiment of the ventilator, in which the receptacle 7 with interface 6 is arranged on a cable 25 in the depression 9. The cable 25 is designed such that the receptacle 7 with interface 6 can be pulled at least partially through the opening 11 out of the depression 9 in order to connect a data transfer stick 19 or a data storage stick 20 to the interface 6 or to remove it again. For example, the depression 9 additionally has a device by which a data transfer stick 19 or a data storage stick 20 connected to the interface 6 is retained in the depression 9. It is thus possible, for example, to prevent unintended movements of the data transfer stick 19 or of the data storage stick 20 that might also lead to accidental separation from the interface. For example, the cable 25 is guided through the base 8 into the interior of the ventilator so that the base is sealed off around the cable 25, such that the transition of the cable 25 into the interior of the ventilator has a protection against spray water and against touching.

In an alternative or supplementary embodiment, the base 8 of the depression 9 can also be formed with a passage 35 through which a line of the data transfer stick 19 is guided which is connected to an interface 6 or plug connection 36 directly on an electronic circuit board 37 of the ventilator.

Figure 15:
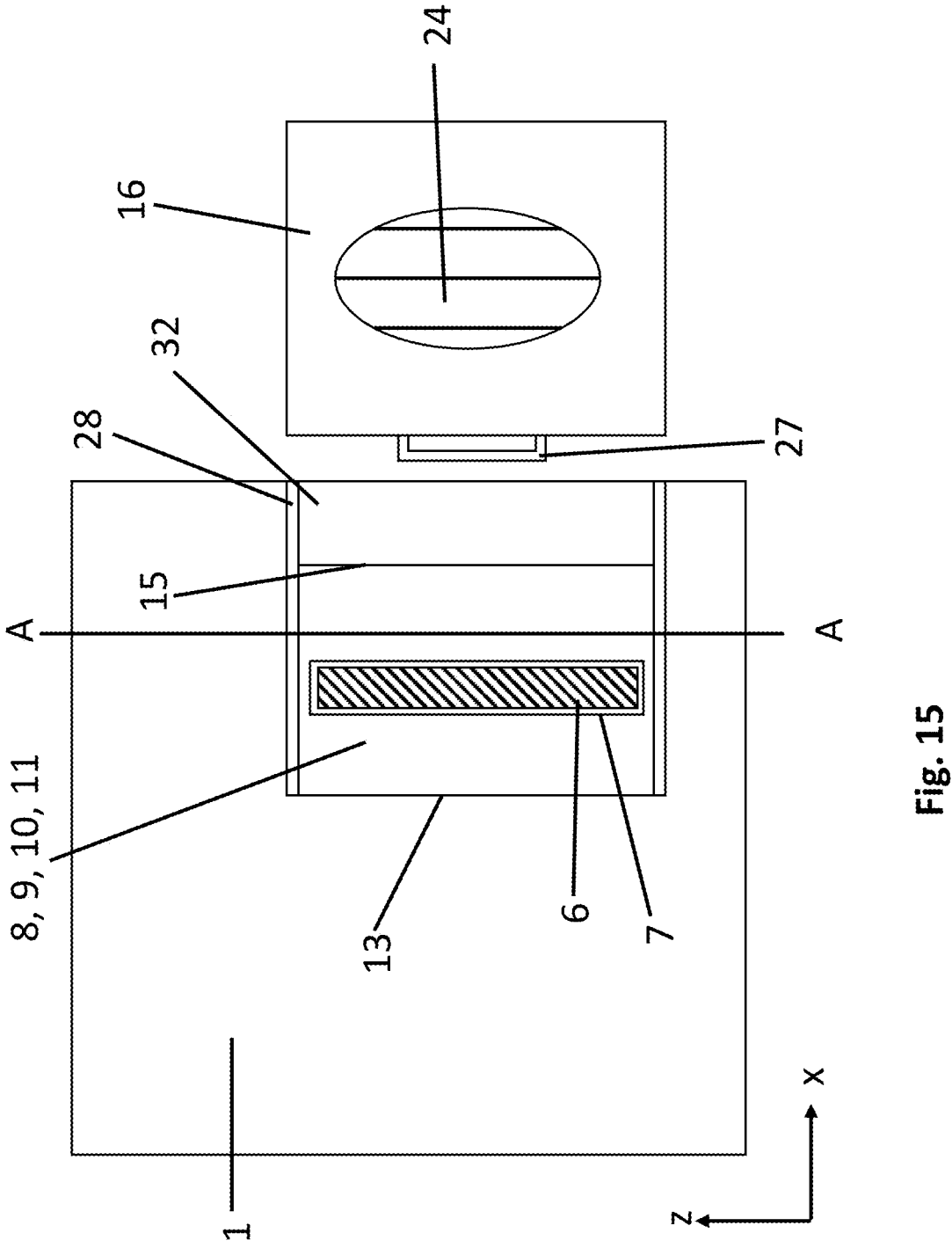
FIG. 15 shows a plan view of an illustrative embodiment of the ventilator, with a lid 16 designed as a slide.

The lid 16 can also be designed, for example, as a slide, as is shown in an illustrative embodiment in FIG. 15. In the embodiment shown, the opening 11 for example extends only in the surface 31 of the housing 1. The lid 16 designed as a slide is in this case guided on at least one guide rail 28 which is mounted on at least one circumferential wall 12, 13, 14, 15 in the region of the opening 11. For example, the lid 16 is equipped with a closure device 27, for which a mating piece (not shown or described in any further detail) is mounted in the housing 1. The closure device 27 has the effect that the lid 16, in the closed state, sits firmly on the opening 11. The closure device 27 can be configured, for example, such that electronic locking takes place if a data transfer stick 19 or a data storage stick 20 is plugged into the interface 6 and the lid 16 is closed. If, for example, the lid 16 is configured such that it closes flush with the housing surface 31, with the depression 9 arranged at a spacing from the housing edge 18, a shoulder 32 for example is formed on one of the housing edges 18, which shoulder 32 is set lower in relation to the housing surface 31. This shoulder 32 is set lower such that the lid 16 can be pushed on the guide rails over the opening 11 and thus closes flush with the housing surface.

In an illustrative embodiment, a surface structuring 24 is applied to the lid 16. This surface structuring is configured, for example, such that the sliding resistance between for example the fingers and the lid 16 is increased.

Figure 16:
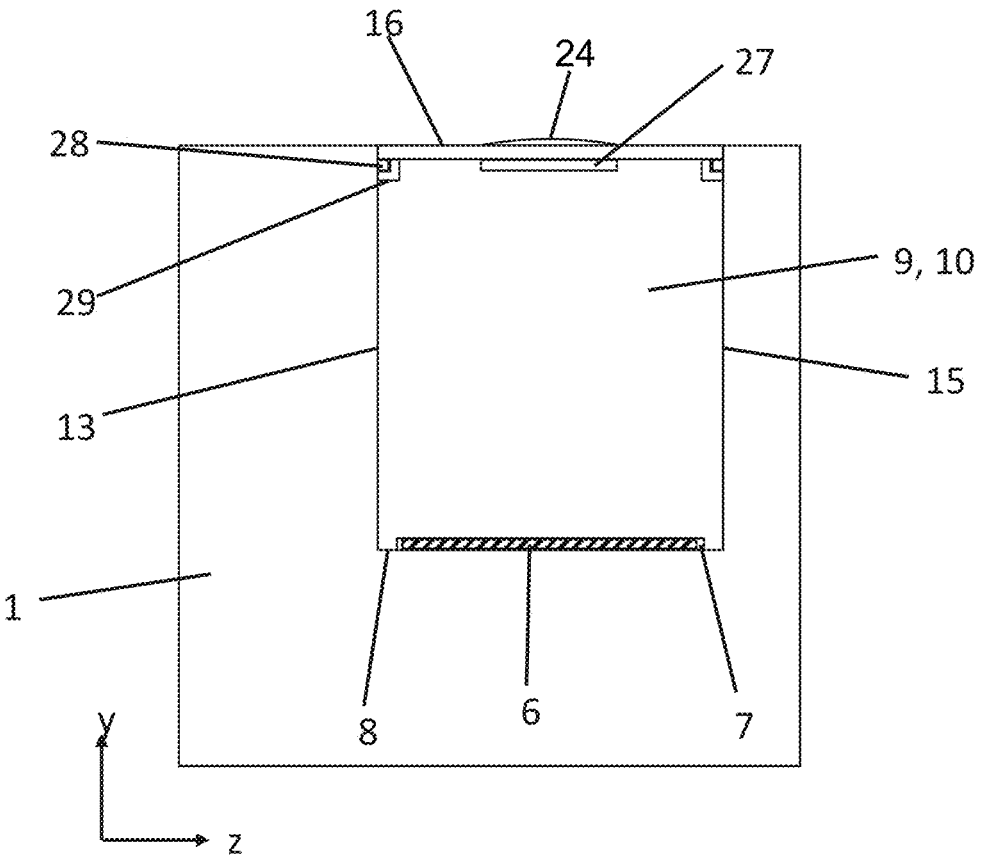
FIG. 16 shows cross section A-A through the housing from FIG. 15, with a lid 16 which is designed as a slide and which is partially closed.

FIG. 16 shows the cross section A-A through the illustrative embodiment of the housing 1 with the lid 16 designed as a slide. For example, guide rails 28 are mounted on the circumferential walls 13 and 15. For the positioning of the lid 16, slide elements 29 matching the guide rails 28 are mounted on the lid 16. The slide elements 29 can additionally perform a retaining function for the lid, e.g. when the depression 9 is mounted on the underside of the ventilator and the lid 16 is intended to be secured against falling out.

Figure 17:
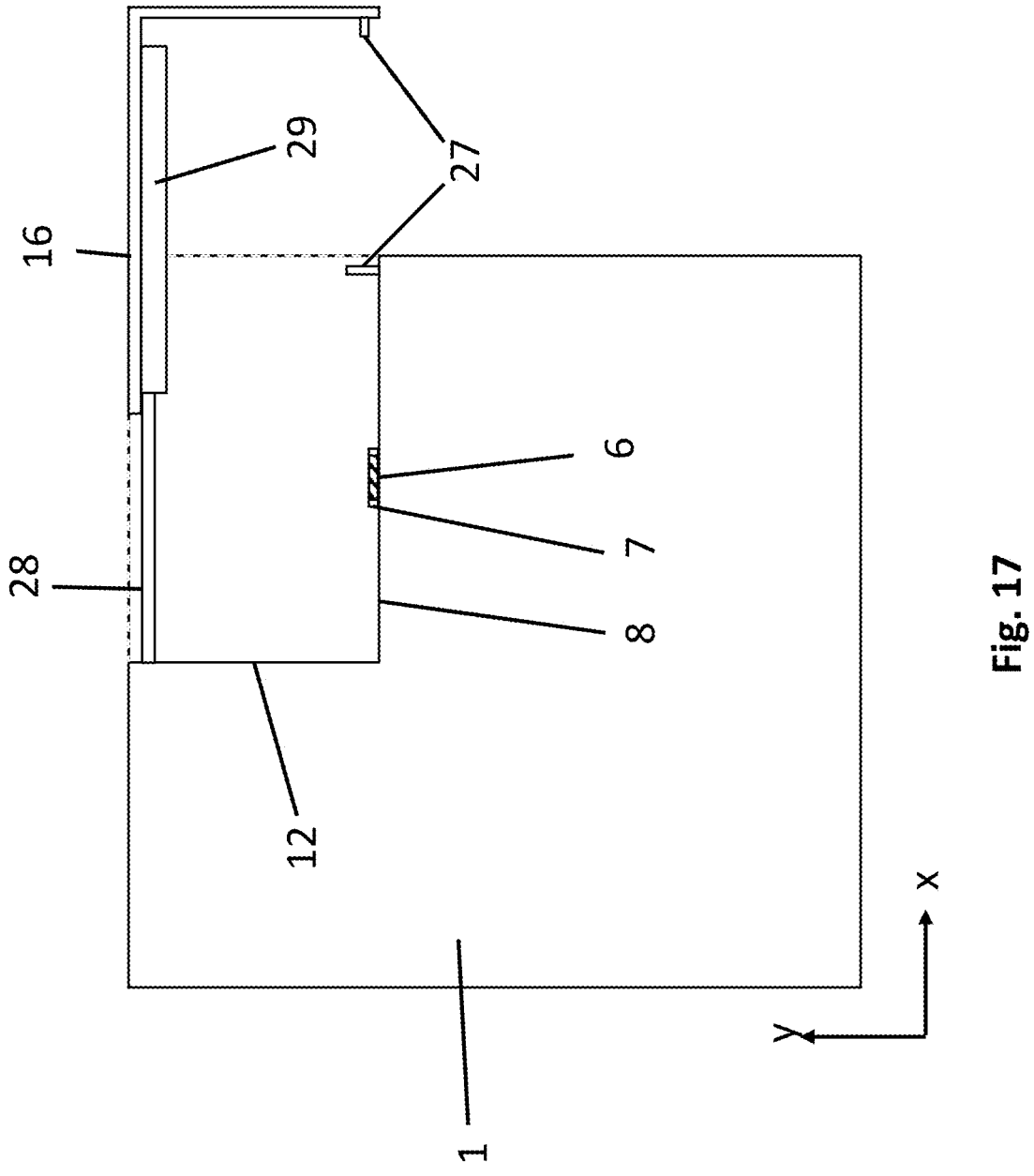
FIG. 17 shows a cross section through an illustrative embodiment of the ventilator, with the depression 9 as part of the outer face 30 in the housing edge 18 and with the lid 16 designed as a slide.

FIG. 17 shows an illustrative embodiment of the housing 1 and of the lid 16, wherein the depression 9 in the housing 1 is part of one of the housing edges 18 and extends partially over an outer face 30. On two mutually opposite circumferential walls, guide rails 28 are mounted with which the lid 16 can be guided over the slide elements 29. For this purpose, closure devices 27 are mounted on the lid 16 and for example on the base 8 of the depression 9 and together permit a locking, for example, of the lid 16 to the housing 1. The locking can be triggered automatically for example, when the lid 16 is closed and a data transfer stick 19 or a data storage stick 20 is connected to the interface 6 arranged for example at the base 8. It would be possible for the locking to be canceled, for example, by an authentication on the ventilator. A simple latching of the closure device 27 of the housing 1 in the closure device 27, or vice versa, is also conceivable for example. In this case, for example, the lid 16 could also be removed without an authentication being needed on the ventilator, for example. In other illustrative embodiments, the closure devices 27 are designed such the lid 16 can be closed or locked with the aid of a key, for example.

The use, for example the startup, of a data transfer stick 19 after connection to the interface 6 may also require an authentication. If a data transfer stick 19 is connected to the interface 6, the stick 19 can for example begin data transfer only when this is enabled or authenticated via the ventilator. In some embodiments, a one-off enabling suffices after the connection of data transfer stick 19 to interface 6.

Figure 18:
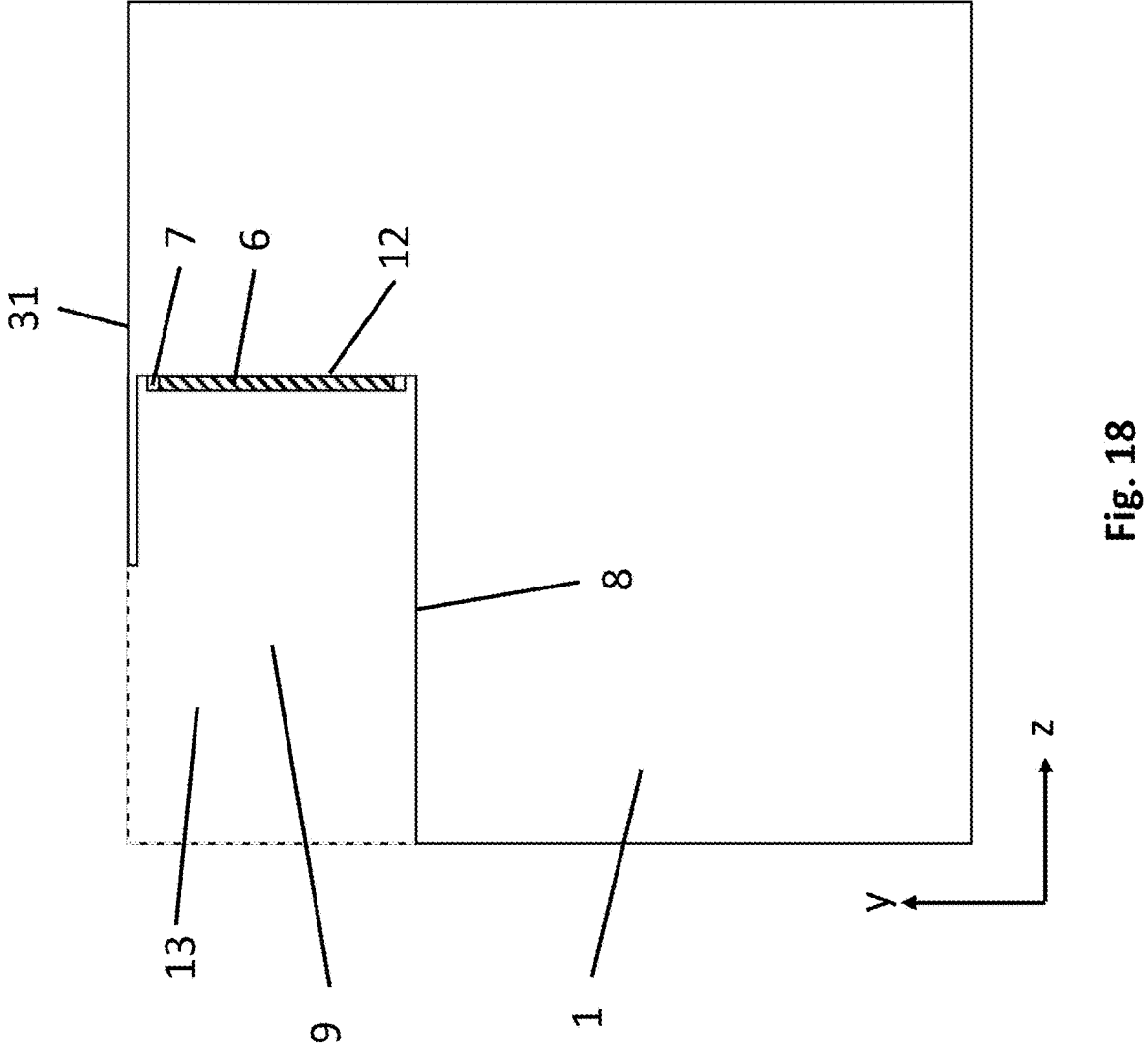
FIG. 18 shows a cross section through an illustrative embodiment of the ventilator, with the receptacle 7 with the interface 6 arranged in a circumferential wall and a subregion of the depression 9 concealed by the housing surface 31.

If the receptacle 7 with the interface 6 is arranged for example in one of the circumferential walls 12, 13, 14, 15, as is shown by way of example in FIG. 18, a subregion of the depression 9 can be concealed by the housing surface 31. For example, the region of the depression 9 in which the receptacle 7 with the interface 6 is arranged in one of the circumferential walls can be concealed by the housing surface 31.

Figure 19:
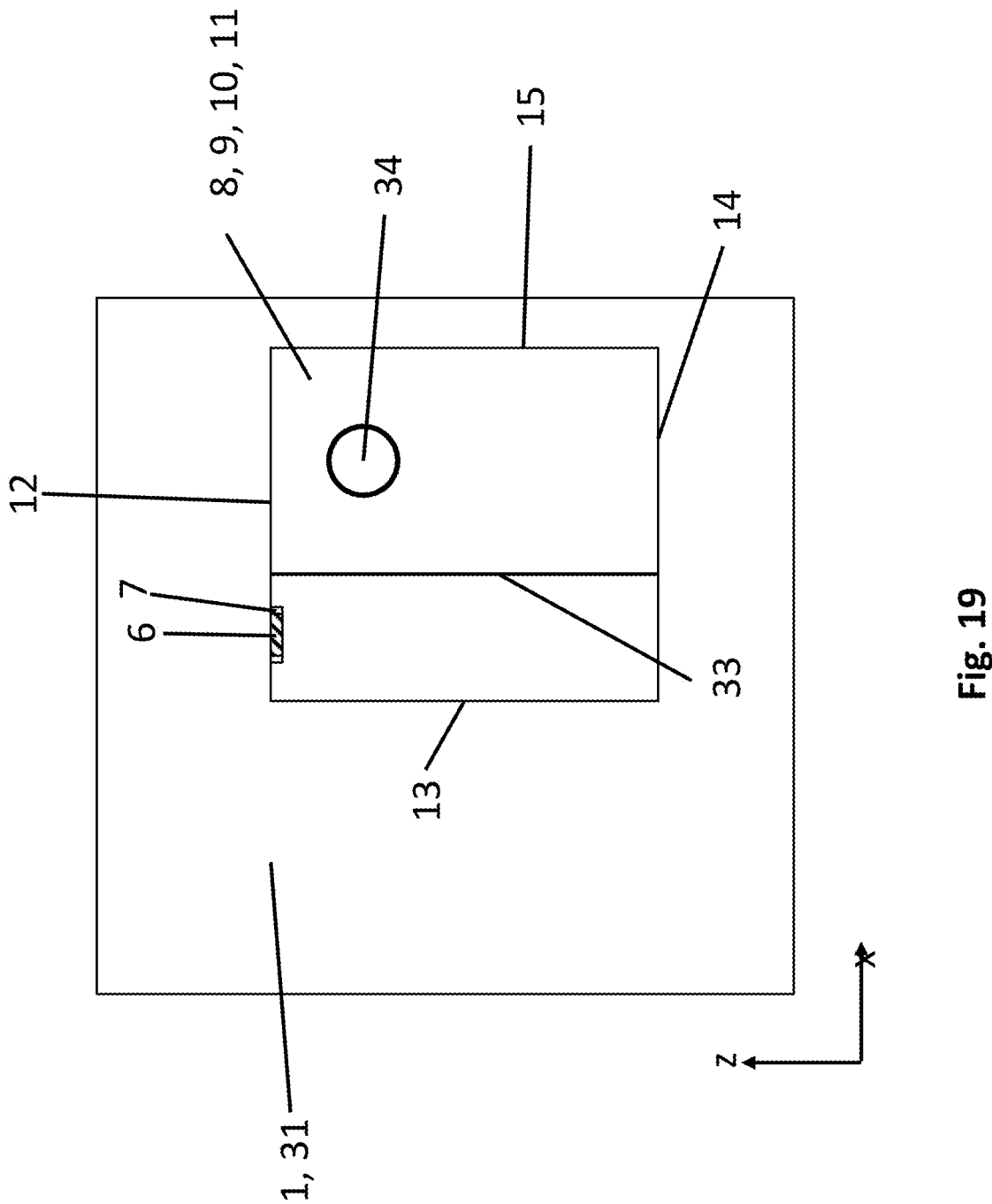
FIG. 19 shows a cross section through an illustrative embodiment of the housing of the ventilator in which, in addition to the receptacle 7 with the interface 6, a further port 34 is arranged in the depression 9.

FIG. 19 shows an illustrative embodiment of the housing 1 in which, in addition to the receptacle 7 with the interface 6, a further port 34 for example is arranged in the depression 9. In the embodiment shown in FIG. 19, the receptacle 7 with the interface 6 is arranged for example on the circumferential wall 12, although it can also be arranged in one of the other circumferential walls 13, 14, 15, the base 8 or the lid 16 (not shown here). Similarly, the further port 34 or additional ports or components can be mounted in the base 8 or at least one of the circumferential walls 12, 13, 14, 15 or the lid 16. The port 34 can be designed, for example, such that an $O_2$ measurement cell can be attached. Other functions of the port 34 are also possible, for example for the attachment of a battery or of other analysis devices or medical devices. The number and the function of further ports 34 or of other components (not described in any further detail) are not limited by the stated examples. It is therefore to be understood that, in addition to the described interface 6, further components and ports, not limited in number and function, can be arranged in the depression 9. For example, the region of the interface 6 is at least partially spatially separated by a partition wall 33 from the region with the additional port 34. For example, the partition wall 33 can have a height such that the partition wall 33 ends flush with the housing surface 31. In some embodiments, the height of the partition wall 33 is for example chosen such that the partition wall 33 does not end flush with the housing surface 31. For example, the partition wall 33 has means or is designed for shielding against radiofrequency waves and electrical fields. For example, the partition wall 33 can also have means or be designed such that electrical fields and sources are permitted only in one preferred direction. In the case of an arrangement of several ports 34 and/or components in addition to the interface 6, further partition walls 33 can also at least partially spatially separate the respective regions from one another.

An example of an alternative configuration of the embodiment shown in FIG. 19 comprises, instead of an interface 6 with receptacle 7 directly in the depression 9, a passage 35 for a line (for example a cable) from the data transfer stick 19 to an attachment point 36 of the interface 6 on an electronic circuit board 37 (not shown) of the ventilator. The passage 35 is for example arranged and configured such that the attachment point 36 is reachable through the passage 35, the data transfer stick 19 can be placed in the depression 9 and the data transfer stick 19 can be connected to the attachment point 36 of the interface 6 via a line. In some embodiments, a line can also be connected to the attachment point 36 of the interface 6, such that the line constitutes a lengthening of the interface 6, as is shown for example by the cable 25 in FIG. 14.

To sum up, the present invention provides:
1. A ventilator which comprises a housing, at least one respiratory gas source, at least one control system and at least one interface, wherein the housing comprises a receptacle for the at least one interface, and the receptacle is arranged with the interface in a depression of the housing, wherein the depression is designed as a well, and the well has an opening, wherein at least two circumferential walls extend from the opening, in a direction of an interior of the ventilator, as far as to a base, and wherein the receptacle is arranged with the interface in a region of the base or of a circumferential wall of the depression.

2. The ventilator of item 1, wherein the depression is closable by a lid.

3. The ventilator of item 2, wherein at least one circumferential wall comprises guide elements for guiding a data transfer stick and/or a data storage stick and supporting same in a mounted state.

4. The ventilator of item 2, wherein the depression is closed by a lid that closes substantially flush with the housing.

5. The ventilator of item 2, wherein the lid is arranged movably relative to the housing and is secured on the housing.

6. The ventilator of item 2, wherein the lid comprises at least one fitting or a surface structuring in order to make it easier to open the lid.

7. The ventilator of item 2, wherein a mechanism is installed in the housing and/or a circumferential wall, which mechanism at least partially opens the lid when pressure is applied and returns it again to a starting position when renewed pressure is applied.

8. The ventilator of at least one of the preceding items, wherein the interface comprises a protection against spray water and against touching.

9. The ventilator of at least one of the preceding items, wherein the receptacle with the interface, and the depression are sealed off from the interior of the ventilator.

10. The ventilator of item 2, wherein the lid can be closed using a tool.

11. The ventilator of item 2, wherein the lid is designed as a slide.

12. The ventilator of item 2, wherein the lid, in a closed state, latches in a corresponding device in the circumferential walls and/or a housing edge and/or in/on the housing.

13. The ventilator of at least one of the preceding items, wherein the depression is arranged in an outer face of the housing, at a distance from the housing edge.

14. The ventilator of at least one of the preceding items, wherein the interface permits contacting with a large number of different data transfer sticks and/or a large number of different data storage sticks.

15. The ventilator of at least one of the preceding items, wherein the receptacle with the interface is recessed in the housing in such a way that a data transfer stick plugged in the receptacle and in the interface can be arranged fully in the depression and terminates at most flush with the surface of the housing but does not protrude beyond the housing surface.

16. The ventilator of at least one of the preceding items, wherein the depression comprises one or more engagement regions for fingers and/or thumbs for allowing a data transfer stick and/or a data storage stick to be pulled easily away from the interface.

17. The ventilator of at least one of the preceding items, wherein the interface and/or the receptacle and/or the depression comprises a removal device with a reset function, and a data transfer stick or a data storage stick is guided, by actuating the removal device, into a position in which it no longer terminates flush with the housing or is arranged inside the housing but instead at least partially protrudes from the housing.

18. The ventilator of at least one of the preceding items, wherein the interface electrically and optionally mechanically connects a data transfer stick to an electronic circuit board present in the ventilator, directly or via a cable connection, and wherein the interface is connected electrically conductively to a control unit of the ventilator and is configured for communication of data signals with the ventilator.

19. The ventilator of at least one of the preceding items, wherein the interface comprises a continuous current contact and/or an automatic current contact, wherein the automatic current contact is assigned a sensor which is designed to detect a mechanical occupancy of the interface.

20. The ventilator of at least one of the preceding items, wherein a data transfer stick is designed as an insert module which can be inserted into the receptacle and plugged into the interface, wherein the interface, through a connection of the data transfer stick, constitutes a transmitter/receiver for establishing a wireless connection.

21. The ventilator of at least one of the preceding items, wherein access to data of a data transfer stick located in the interface is protected by password and/or hardware encoding.

22. The ventilator of at least one of the preceding items, wherein the interface and/or the receptacle and/or the base and/or the depression and/or the well and/or at least one circumferential wall comprises elements and/or is configured to prevent or attenuate electrical fields and radio-frequency waves in at least one blocking direction.

23. The ventilator of item 2, wherein the lid can be locked electronically, and wherein the electronic locking of the lid can be canceled by an authentication.

24. The ventilator of at least one of the preceding items, wherein the receptacle with the interface is arranged movably in the depression.

25. The ventilator of at least one of the preceding items, wherein at least one further component and/or at least one further port is arranged in the depression in addition to the interface, wherein a region of the interface in the depression is at least partially spatially separated from the at least one further component and/or port by an at least partially formed partition wall.

26. A system for establishing a wireless connection, wherein the system comprises at least one ventilator, at least one interface, at least one data transfer stick and at least one lid, wherein the interface is arranged in a depression, and the data transfer stick is connected removably in the depression to the interface, and wherein the depression can be closed with the at least one lid.

LIST OF REFERENCE NUMERALS 1 housing
2 respiratory gas source
3 control system
4 control system
5 control system
6 interface
7 receptacle
8 base
9 depression
10 well
11 opening
12 circumferential wall
13 circumferential wall 14 circumferential wall
15 circumferential wall
16 lid
    17 peripheral seal
    18 housing edge
    19 data transfer stick
    20 data storage stick
    21 removal device
    22 engagement region
    23 fitting
    24 surface structuring
    25 cable
    26 hinge
    27 closure device
    28 guide rail
    29 slide element
    30 outer face
    31 housing surface
    32 shoulder
    33 partition wall
    34 port
    35 passage
    36 attachment point
    37 circuit board
    What is claimed is:

1. A ventilator, wherein the ventilator comprises a housing, at least one respiratory gas source, at least one control system and at least one interface, wherein the housing comprises a receptacle for the at least one interface, and the receptacle is arranged with the interface in a depression of the housing, wherein the depression is designed as a well, and the well has an opening, wherein at least two peripheral walls extend from the opening, in a direction of an interior of the ventilator, as far as to a base, and wherein the receptacle is arranged with the interface in a region of the base or of a peripheral wall of the depression.

2. The ventilator of claim 1, wherein the depression is closable by a lid.

3. The ventilator of claim 1, wherein at least one peripheral wall comprises guide elements for guiding a data transfer stick and/or a data storage stick and supporting same in a mounted state.

4. The ventilator of claim 2, wherein the lid is arranged movably relative to the housing and is secured on the housing.

5. The ventilator of claim 2, wherein the lid comprises at least one fitting or a surface structuring in order to make it easier to open the lid.

6. The ventilator of claim 2, wherein a mechanism is installed in the housing and/or a peripheral wall, which mechanism at least partially opens the lid when pressure is applied and returns it again to a starting position when renewed pressure is applied.

7. The ventilator of claim 1, wherein the receptacle with the interface, and the depression are sealed off from an interior of the ventilator.

8. The ventilator of claim 2, wherein the lid can be closed using a tool.

9. The ventilator of claim 2, wherein the lid is designed as a slide.

10. The ventilator of claim 2, wherein the lid, in a closed state, latches in a corresponding device in the peripheral walls and/or a housing edge and/or in/on the housing.

11. The ventilator of claim 1, wherein the depression is arranged in an outer face of the housing, at a distance from a housing edge.

12. The ventilator of claim 1, wherein the receptacle with the interface is recessed in the housing in such a way that a data transfer stick plugged in the receptacle and in the interface can be arranged fully in the depression and terminates at most flush with a surface of the housing but does not protrude beyond the housing surface.

13. The ventilator of claim 1, wherein the interface and/or the receptacle and/or the depression comprises a stick positioning device, and a data transfer stick or a data storage stick is guided, by actuating the stick positioning device, into a position in which it no longer terminates flush with the housing or is arranged inside the housing but instead at least partially protrudes from the housing.

14. The ventilator of claim 1, wherein the interface electrically and optionally mechanically connects a data transfer stick to an electronic circuit board present in the ventilator, directly or via a cable connection, and wherein the interface is connected electrically conductively to a control unit of the ventilator and is configured for communication of data signals with the ventilator.

15. The ventilator of claim 1, wherein a data transfer stick is designed as an insert module which can be inserted into the receptacle and plugged into the interface, wherein the interface, through a connection of the data transfer stick, constitutes a transmitter/receiver for establishing a wireless connection.

16. The ventilator of at claim 1, wherein the interface and/or the receptacle and/or the base and/or the depression and/or the well and/or at least one peripheral wall comprises elements and/or is configured to prevent or attenuate electrical fields and radio-frequency waves in at least one blocking direction.

17. The ventilator of claim 1, wherein the receptacle with the interface is arranged movably in the depression.

18. The ventilator of claim 1, wherein the depression further comprises at least one component and/or at least one port in addition to the interface, and wherein a region of the interface in the depression is at least partially spatially separated from the at least one further component and/or port by an at least partially formed partition wall.

19. A system for establishing a wireless connection, wherein the system comprises the ventilator of claim 1, at least one data transfer stick and at least one lid, wherein the data transfer stick is connected removably in the depression to the interface, and wherein the depression can be closed with the at least one lid.

20. The ventilator of claim 1, wherein the interface comprises protection against spray water and contact.

* * * * *